United States Patent
Kuroda et al.

(10) Patent No.: US 7,164,040 B2
(45) Date of Patent: Jan. 16, 2007

(54) PROCESS FOR PRODUCTION OF HIGH-PURITY CRYSTALS OF GLYCOLIC ACID

(75) Inventors: Yoshito Kuroda, Kurashiki (JP); Harumi Watanabe, Kurashiki (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 82 days.

(21) Appl. No.: 10/500,882

(22) PCT Filed: Jan. 29, 2003

(86) PCT No.: PCT/JP03/00858

§ 371 (c)(1), (2), (4) Date: Jul. 7, 2004

(87) PCT Pub. No.: WO03/064366

PCT Pub. Date: Aug. 7, 2003

(65) Prior Publication Data

US 2005/0020853 A1 Jan. 27, 2005

(30) Foreign Application Priority Data

Jan. 29, 2002 (JP) .............................. 2002-020037

(51) Int. Cl.
 *C07C 51/42* (2006.01)
(52) U.S. Cl. .................................... 562/580
(58) Field of Classification Search ............... 562/579, 562/580, 587; 560/180, 189
See application file for complete search history.

(56) References Cited

FOREIGN PATENT DOCUMENTS

| JP | 62-77349 A | 4/1987 |
|---|---|---|
| JP | 62-077349 A | 4/1987 |
| JP | 05-092102 A | 4/1993 |
| JP | 5-92102 A | 4/1993 |
| JP | 8-268955 A | 10/1996 |
| JP | 08-268955 A | 10/1996 |
| JP | 09-002998 A | 1/1997 |
| JP | 9-2998 A | 1/1997 |
| WO | 199205138 * | 4/1992 |
| WO | WO 92/5138 A1 | 4/1992 |
| WO | WO 00/56693 A1 | 9/2000 |

OTHER PUBLICATIONS

P. Stephenson, "The Structure of the Digitised Line: with Applications in Line Drawing and Ray Tracing in Computer Graphics", PhD Thesis, James Cook University of North Queensland, Australia, 1998.
P. Stephenson and B. Litgow, "Making the DDA run: Two-dimensional ray traversal using runs and runs of runs", 24th Australian Computer Science Proceedings, Gold Coast Australia, Feb. 2001, 23(1): 177-183.
P. Stephenson and B. Litow, "Why Step When You Can Run? Interactive Line Digitization Algorithms Based on Hierarchies of Runs", IEEE Computer Graphics and Applications, Nov.-Dec. 2000 pp. 76-84.
P. Stephenson and B. Litow, "Running the line: Line drawing using runs and runs of runs", Computers and Graphics 25 (2001) pp. 681-690.
V. Boyer and J. J. Bourdin, "Fast Lines: a Span by Span Method", EuroGraphics '99 vol. 18, No. 3, The Eurographics Association and Blackwell Publishers, 1999.
E. J. Lee and L. F. Hodges, "Run-Based Multi-Point Line Drawing"1993.
J. Amanatides and A. Woo, A Fast Voxel Traversal Algorithm for Ray Tracing:, EuroGraphics, 1987.
M. Levoy, "Efficient Ray Tracing of Volume Data" , Apr. 1989.
J. E. Bresenham, "An incremental algorithm for digital plotting", ACM National Conference, Aug. 1963.
G. B. Reggiori, "Digital computer transformations for irregular line drawings", Technical Report, New York University, Apr. 1972, pp. 403-422.
J. D. Foley, A. Van Dam, S. K. Feiner, J. F. Hughes, Introduction to Computer Graphics, Addison-Wesley, 1994, pp. 70-80.
J. D. Foley, A Van Dam, S. K. Feiner, J. F. Hughes, Computer Graphics: Principles and Practice, Second Edition in C. Addison-Wesely, 1990 pp. 72-83.

* cited by examiner

*Primary Examiner*—Thurman K. Page
*Assistant Examiner*—Karl Puttlitz
(74) *Attorney, Agent, or Firm*—Birch, Stewart, Kolasch & Birch, LLP

(57) ABSTRACT

A method for producing high purity glycolic acid crystals, which comprises the steps of: (1) providing an aqueous glycolic acid solution (A) which has (a) a water content of from 5 to 20% by weight, (b) a calculated monomeric glycolic acid weight ratio (ratio of the total weight of the monomeric glycolic acid and the component monomeric glycolic acid of the glycolic acid condensation product to the weight of the aqueous glycolic acid solution (A)) of from 0.60 to 1.00 and (c) a monomeric glycolic acid content of from 20 to 57% by weight; (2) depositing glycolic acid crystals from the solution (A); and (3) separating the deposited glycolic acid crystals from the solution (A).

5 Claims, No Drawings

PROCESS FOR PRODUCTION OF HIGH-PURITY CRYSTALS OF GLYCOLIC ACID

BACKGROUND OF THE INVENTION

1. Field of the Invention

The present invention relates to a method for producing high purity glycolic acid crystals from an aqueous glycolic acid solution. More particularly, the present invention is concerned with a method for producing high purity glycolic acid crystals from an aqueous glycolic acid solution, which comprises the steps of: providing an aqueous glycolic acid solution which contains monomeric glycolic acid and a glycolic acid condensation product, and has a specific water content, a specific calculated monomeric glycolic acid weight ratio (ratio of the total weight of the monomeric glycolic acid and the component monomeric glycolic acid of the glycolic acid condensation product to the weight of the aqueous solution) and a specific monomeric glycolic acid content; depositing glycolic acid crystals from the aqueous glycolic acid solution; and separating the deposited glycolic acid crystals from the aqueous glycolic acid solution. By the method of the present invention, it becomes possible to produce high purity glycolic acid crystals easily and in high yield on a commercial scale, which high purity glycolic acid crystals are essential for producing a glycolic acid polymer having a high molecular weight.

2. Prior Art

Conventionally, glycolic acid has been used as an important component of cosmetics, a hair dying agent, a shampoo, detergents (e.g., a detergent for domestic use and a detergent for industrial use), a metal treating agent, a tanning agent and the like. In recent years, glycolic acid is also widely used as a raw material for various chemical products, a raw material for various synthetic resins and the like.

It is required that glycolic acid for use as the above-mentioned raw materials have high purity. The reason for this is explained below, taking as an example the case where glycolic acid is used as a raw material for a synthetic resin, wherein the glycolic acid is required to have an extremely high purity.

In general, for obtaining a polyester resin comprised mainly of glycolic acid monomer units, which exhibits a mechanical strength sufficient for general use, it is desired that the polyester resin have a weight average molecular weight of 150,000 or more (see, for example, Unexamined Japanese Patent Application Laid-open Specification No. Hei 11-130847 (corresponding to WO99/19378)). When such a polyester resin is produced by polycondensation of a raw material mixture containing glycolic acid as a main component thereof, care must be taken as to the following points. Glycolic acid is a self-condensing compound having, in a molecule thereof, one carboxyl group and one alcoholic hydroxyl group. Therefore, when the raw material mixture contains, as an impurity, a carboxylic acid having no alcoholic hydroxyl group or an alcohol having no carboxyl group, such an impurity inevitably reacts with glycolic acid and/or a polycondensation product of glycolic acid, thereby terminating the growth of the polymer chain. As a result, a polyester resin having a high molecular weight cannot be obtained. Further, when the raw material mixture contains a salt as an impurity, the mechanical property of the polyester resin obtained is markedly lowered. Accordingly, when the production of a polyester resin is performed by poly-condensation of a raw material mixture containing glycolic acid as a main component thereof, it is necessary that the glycolic acid have a high purity. In general, the glycolic acid is required to have a purity as high as 99.9% by weight or more.

As conventional methods for producing glycolic acid on a commercial scale, there can be mentioned:

(a) a method in which glycolic acid is produced by reacting formaldehyde, carbon monoxide and water in the presence of an acid catalyst; and (b) a method in which chloroacetic acid is saponified.

In each of the above-mentioned methods (a) and (b), glycolic acid is obtained in the form of an aqueous solution thereof. However, in each of these methods, a carboxylic acid and an alcohol are by-produced in large amounts, and a salt is by-produced in an amount such that the mechanical properties of a resin produced from the glycolic acid become markedly low. Therefore, for obtaining a high purity glycolic acid which can be used as a raw material for producing a resin having a high molecular weight, it is necessary that the aqueous glycolic acid solution be subjected to purification.

As an example of a generally employed purification method, there can be mentioned a distillation method. When the purification of glycolic acid is performed by distillation method, a distillate containing glycolic acid is obtained, and the obtained distillate is cooled and solidified to thereby obtain high purity glycolic acid crystals. However, it is difficult to obtain high purity glycolic acid crystals by the distillation of the above-mentioned aqueous solution of glycolic acid. The reason for this is as follows. Glycolic acid has low volatility. Further, glycolic acid is susceptible to a polycondensation reaction under the distillation conditions, so that a condensation product which is difficult to distill is formed. Therefore, it is difficult to obtain high purity glycolic acid crystals by the distillation method.

For these reasons, there have been proposed methods (other than the distillation method) for producing high purity glycolic acid crystals from an aqueous glycolic acid solution.

For example, Unexamined Japanese Patent Application Laid-open Specification No. Hei 8-268955 (corresponding to EP 733616 and BR 9601063) describes a method in which water is removed from an aqueous glycolic acid solution under specific conditions so as to form a molten product containing glycolic acid, and a crystallization agent is added to the formed molten product, followed by cooling to produce glycolic acid crystals. However, when it is intended to produce high purity glycolic acid crystals by this method, it is necessary to purify, in advance, the aqueous glycolic acid solution to a very high degree by a method, such as electrodialysis, solvent extraction or the like. Therefore, when it is intended to produce high purity glycolic acid crystals by this method, many complicated steps become necessary and, thus, the entire process becomes very cumbersome.

As another method for producing glycolic acid crystals from an aqueous glycolic acid solution, Japanese Patent Application Prior-to-Examination Publication (Tokuhyo) No. Hei 6-501268 (corresponding to WO92/05138 and EP 552255) describes a method in which an aqueous glycolic acid solution containing about 62.4% by weight of monomeric glycolic acid, about 8.8% by weight of dimeric glycolic acid, about 2.2% by weight of diglycolic acid, about 2.2% by weight of methoxyacetic acid, and about 0.24% by weight of formic acid is used as a starting material, and is cooled to −25 to 10° C., followed by addition of high purity glycolic acid crystals, as seed crystals, in an amount sufficient to induce the crystallization of glycolic acid in the solution, thereby obtaining glycolic acid crystals. In this patent document, it is described that high purity glycolic acid crystals can be obtained depending on the conditions for crystallization of glycolic acid. However, when it is intended to obtain high purity glycolic acid crystals in high yield by the method described in the patent document, a very long period of time is needed for crystallization of glycolic acid and, thus, the method becomes economically disadvantageous.

Further, the above-mentioned patent document also describes a method in which, in an attempt to improve the yield of the glycolic acid crystals, a mother liquor after the separation of glycolic acid crystals is concentrated, and the resultant concentrated mother liquor is subjected to a further crystallization. However, this method has a problem in that the purity of glycolic acid crystals recovered after the further crystallization is markedly low.

Further, there is also known a method for producing high purity glycolic acid crystals, which, however, is difficult to practice on a commercial scale. Specifically, in this method, crude glycolic acid crystals are produced and dissolved in an organic solvent, such as acetone, and the resultant solution is allowed to stand while cooling the solution to −10° C., thereby obtaining high purity glycolic acid crystals. Further, Unexamined Japanese Patent Application Laid-open Specification No. Hei 5-92102 describes a method in which crude glycolic acid crystals are dissolved in an organic solvent, such as acetone, to obtain a solution, followed by mixing thereof with high pressure gas, thereby obtaining high purity glycolic acid crystals. However, these methods are difficult to practice on a commercial scale for the following reasons. When it is intended to practice any of the above-mentioned methods on a commercial scale, the use of a large amount of a harmful organic solvent is necessary and the whole amount of the solvent used must be removed or recovered by distillation. Therefore, from the viewpoint of protection of environment and economy, it is impossible to practice the above-mentioned methods on a commercial scale.

Thus, by the conventional methods, it has been impossible to produce high purity glycolic acid crystals from an aqueous glycolic acid solution easily and in high yield on a commercial scale.

SUMMARY OF THE INVENTION

In this situation, the present inventors have made extensive and intensive studies with a view toward developing a method for producing high purity glycolic acid crystals from an aqueous glycolic acid solution easily and in high yield on a commercial scale. As a result, it has unexpectedly been found that, by subjecting a specific aqueous glycolic acid solution to crystallization, it becomes possible to produce high purity glycolic acid crystals easily and in high yield on a commercial scale, which crystals are substantially free of impurities, such as carboxylic acids other than glycolic acid, alcohols and salts. The specific aqueous glycolic acid solution contains monomeric glycolic acid and a glycolic acid condensation product, and has a specific water content, a specific calculated monomeric glycolic acid weight ratio (ratio of the total weight of the monomeric glycolic acid and the component monomeric glycolic acid of the glycolic acid condensation product to the weight of the aqueous solution) and a specific monomeric glycolic acid content. Based on this novel finding, the present invention has been completed.

Accordingly, it is an object of the present invention to provide a method for producing high purity glycolic acid crystals from an aqueous glycolic acid solution easily and in high yield on a commercial scale.

The foregoing and other objects, features and advantages of the present invention will be apparent from the following detailed description and appended claims.

DETAILED DESCRIPTION OF THE INVENTION

According to the present invention, there is provided a method for producing high purity glycolic acid crystals from an aqueous glycolic acid solution, which comprises the steps of:

(1) providing an aqueous glycolic acid solution (A) containing monomeric glycolic acid and a glycolic acid condensation product, the aqueous glycolic acid solution (A) having the following characteristics (a), (b) and (c):
  (a) a water content of from 5 to 20% by weight,
  (b) a calculated monomeric glycolic acid weight ratio of from 0.60 to 1.00, the calculated monomeric glycolic acid weight ratio being defined as a ratio of the total weight of the monomeric glycolic acid and the glycolic acid condensation product to the weight of the aqueous solution (A), wherein the weight of the glycolic acid condensation product is expressed in terms of the weight of component monomeric glycolic acid of the glycolic acid condensation product, and
  (c) a monomeric glycolic acid content of from 20 to 57% by weight, (2) depositing glycolic acid crystals from the aqueous glycolic acid solution (A), and (3) separating the deposited glycolic acid crystals from the aqueous glycolic acid solution (A).

For easy understanding of the present invention, the essential features and various preferred embodiments of the present invention are enumerated below.

1. A method for producing high purity glycolic acid crystals from an aqueous glycolic acid solution, which comprises the steps of:
   (1) providing an aqueous glycolic acid solution (A) containing monomeric glycolic acid and a glycolic acid condensation product, the aqueous glycolic acid solution (A) having the following characteristics (a), (b) and (c):
     (a) a water content of from 5 to 20% by weight,
     (b) a calculated monomeric glycolic acid weight ratio of from 0.60 to 1.00, the calculated monomeric glycolic acid weight ratio being defined as a ratio of the total weight of the monomeric glycolic acid and the glycolic acid condensation product to the weight of the aqueous solution (A), wherein the weight of the glycolic acid condensation product is expressed in terms of the weight of component monomeric glycolic acid of the glycolic acid condensation product, and
     (c) a monomeric glycolic acid content of from 20 to 57% by weight,
   (2) depositing glycolic acid crystals from the aqueous glycolic acid solution (A), and
   (3) separating the deposited glycolic acid crystals from the aqueous glycolic acid solution (A).

2. The method according to item 1 above, wherein the deposition of glycolic acid crystals from the aqueous glycolic acid solution (A) in the step (2) is performed at a temperature in the range of from −30 to 50° C.

3. The method according to item 1 or 2 above, wherein the deposition of glycolic acid crystals from the aqueous glycolic acid solution (A) in the step (2) is performed in the presence of glycolic acid crystals as seed crystals.

4. The method according to any one of items 1 to 3 above, which further comprises, after the step (3), the step of:

(4) washing the separated glycolic acid crystals with an aqueous glycolic acid solution (B).
5. The method according to item 4 above, wherein:
the aqueous glycolic acid solution (B) contains monomeric glycolic acid and optionally a glycolic acid condensation product, and
the aqueous glycolic acid solution (B) satisfies the following formulae (I) and (II):

$$0.0055 \times T + 0.3 \leq W \leq 0.0072 \times T + 0.8 \quad (I)$$

and $$-5 \leq T \leq 70 \quad (II)$$

wherein:
W represents a calculated monomeric glycolic acid weight ratio of the aqueous solution (B), the calculated monomeric glycolic acid weight ratio being defined as a ratio of the total weight of the monomeric glycolic acid and the glycolic acid condensation product to the weight of the aqueous solution (B), wherein the weight of the glycolic acid condensation product is expressed in terms of the weight of component monomeric glycolic acid of the glycolic acid condensation product, and
T represents the temperature (°C.) of the aqueous solution (B).

Hereinbelow, the present invention is described in detail.
With respect to the terms used in the present invention, explanations are given below.

The term "glycolic acid crystals" means a crystallized form of monomeric glycolic acid, or a crystallized form of a mixture of monomeric glycolic acid and a glycolic acid condensation product. The term "monomeric glycolic acid" means glycolic acid as a monomer (i.e., compound represented by the formula: HOCH$_2$COOH). The term "glycolic acid condensation product" means a condensation product of a plurality of glycolic acid monomers, wherein two adjacent glycolic acid monomers are bonded to each other through an ester linkage, or a condensation product of a monomeric glycolic acid with a compound other than glycolic acid, wherein the compound other than glycolic acid is bonded to the monomeric glycolic acid through an ester linkage. For example, a glycolic acid dimer represented by the following formula:

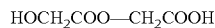
HOCH$_2$COO—CH$_2$COOH is a glycolic acid condensation product. Further, an ester of glycolic acid with lactic acid, which is represented by the following formula:

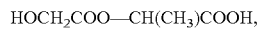
HOCH$_2$COO—CH(CH$_3$)COOH, is also a glycolic acid condensation product. On the other hand, diglycolic acid, which is represented by the following formula:

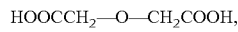
HOOCCH$_2$—O—CH$_2$COOH, and which is a condensation product wherein two glycolic acid monomers are bonded to each other through an ether linkage, is not included in the category of a glycolic acid condensation product. However, when such diglycolic acid is esterified with glycolic acid to form a compound represented by the following formula:

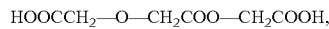
HOOCCH$_2$—O—CH$_2$COO—CH$_2$COOH, such a compound is a glycolic acid condensation product.

The term "aqueous glycolic acid solution" means an aqueous solution of monomeric glycolic acid or an aqueous solution of monomeric glycolic acid and a glycolic acid condensation product.

The "calculated monomeric glycolic acid weight ratio" of the aqueous glycolic acid solution is defined as a ratio of the total weight of the monomeric glycolic acid and the glycolic acid condensation product to the weight of the aqueous solution, wherein the weight of the glycolic acid condensation product is expressed in terms of the weight of component monomeric glycolic acid of the glycolic acid condensation product. Herein, the term "component monomeric glycolic acid" means a monomeric glycolic acid which is obtained by a method in which the above-mentioned glycolic acid condensation product is hydrolyzed using a basic aqueous solution (such as an aqueous sodium hydroxide solution), and the resultant hydrolysis mixture is acidified.

As apparent from the above definition, with respect to a self-condensation product of glycolic acid, the calculated weight thereof in terms of the weight of component monomeric glycolic acid is larger than the actual weight of the glycolic acid self-condensation product. Therefore, when most of the glycolic acid contained in the aqueous glycolic acid solution is present in the form of a self-condensation product of glycolic acid, the calculated monomeric glycolic acid weight ratio of the aqueous glycolic acid solution may exceed 1.

The calculated monomeric glycolic acid weight ratio of the aqueous glycolic acid solution can be obtained as follows. The aqueous glycolic acid solution is hydrolyzed using a basic aqueous solution (such as an aqueous sodium hydroxide solution), and the resultant mixture is acidified, thereby obtaining a sample solution. The monomeric glycolic acid concentration of the obtained sample solution is measured by high performance liquid chromatography (HPLC). From the found value of the monomeric glycolic acid concentration, the weight of the monomeric glycolic acid contained in the sample solution is calculated. The ratio of the thus obtained weight of the monomeric glycolic acid contained in the sample solution to the weight of the aqueous glycolic acid solution is defined as the calculated monomeric glycolic acid weight ratio of the aqueous glycolic acid solution.

In the present invention, the aqueous glycolic acid solution may contain one or more types of impurities. Examples of impurities include organic compounds (such as the above-mentioned diglycolic acid and lactic acid) which are by-produced in the course of the glycolic acid synthesis process; and inorganic substances. Examples of inorganic substances include inorganic compounds (such as sodium chloride) which are derived from a reagent used in the glycolic acid synthesis process; and metal cations (e.g., a nickel cation, a chromium cation and a titanium cation) which are dissolved out from the apparatus used in the glycolic acid synthesis process. (More specific examples of impurities are enumerated below). When the aqueous glycolic acid solution contains, as an impurity, an organic compound (such as diglycolic acid, lactic acid or the like) which is capable of forming a condensation product thereof with glycolic acid, such an organic compound may be present independently or in the form of a condensation product thereof with glycolic acid.

The content (% by weight) of the above-mentioned impurity or impurities (i.e., the above-mentioned organic compound(s) and/or the above-mentioned inorganic substance(s)) in the aqueous glycolic acid solution can be measured by the following method. The identification and quantitative determination of an organic compound as an impurity can be performed by the above-mentioned method in which a sample solution obtained by hydrolyzing the aqueous glycolic acid solution is analyzed by high performance liquid chromatography. By this method, even when the aqueous glycolic acid solution contains a condensation product of an impurity (such as diglycolic acid or lactic acid) with glycolic acid, such an impurity is separated from glycolic acid by hydrolyzing the condensation product, so that it is possible to perform the identification and quantitative determination of the impurity by high performance liquid chromatography.

The amount of the above-mentioned inorganic compound as an impurity can be determined as follows. The amounts of a metal cation (such as a sodium cation) and an inorganic anion (such as a chloride anion) which are contained in the aqueous glycolic acid solution are measured respectively. The total of the amounts of the metal cation and the inorganic anion is defined as the amount of the inorganic compound as an impurity. With respect to the method for determining the amount of the above-mentioned ions, there is no particular limitation. Examples of methods for determining the amount of a metal cation (such as a sodium cation) include inductively coupled plasma (ICP) optical emission spectroscopy, atomic absorption analysis, and ion chromatography. On the other hand, examples of methods for determining the amount of an inorganic anion (such as a chloride anion) include ion chromatography.

From the found value of the total weight of the impurities (i.e., the above-mentioned organic compounds and/or inorganic substances), the % by weight of the total of the impurities, based on the weight of the aqueous glycolic acid solution, is calculated, which is defined as the impurity content of the aqueous glycolic acid solution.

The content of the impurities in glycolic acid crystals can be obtained in the same manner as mentioned above. In the present invention, from the found value of the content of the impurities in glycolic acid crystals, the purity of the glycolic acid crystals is calculated by the following formula:

Purity (% by weight) of the glycolic acid crystals=100−(content of the impurities in glycolic acid crystals)

Hereinbelow, the method of the present invention is described.

The method of the present invention is a method for producing high purity glycolic acid crystals from an aqueous glycolic acid solution, which comprises the steps of:

(1) providing an aqueous glycolic acid solution (A) containing monomeric glycolic acid and a glycolic acid condensation product, the aqueous glycolic acid solution (A) having the following characteristics (a), (b) and (c):

(a) a water content of from 5 to 20% by weight, (b) a calculated monomeric glycolic acid weight ratio of from 0.60 to 1.00, the calculated monomeric glycolic acid weight ratio being defined as a ratio of the total weight of the monomeric glycolic acid and the glycolic acid condensation product to the weight of the aqueous solution (A) wherein the weight of the glycolic acid condensation product is expressed in terms of the weight of component monomeric glycolic acid of the glycolic acid condensation product, and (c) a monomeric glycolic acid content of from 20 to 57% by weight, (2) depositing glycolic acid crystals from the aqueous glycolic acid solution (A), and (3) separating the deposited glycolic acid crystals from the aqueous glycolic acid solution (A).

First, explanation is made with respect to step (1) of the method of the present invention.

In step (1), an aqueous glycolic acid solution (A) is provided. With respect to the aqueous glycolic acid solution (A), there is no particular limitation so long as it contains monomeric glycolic acid and a glycolic acid condensation product and has the above-mentioned characteristics (a), (b) and (c). As mentioned above, the aqueous glycolic acid solution (A) may contain impurities.

Hereinbelow, the above-mentioned characteristics (a), (b) and (c) are described.

First, explanation is made with respect to the above-mentioned characteristic (a). In the present invention, the aqueous glycolic acid solution (A) has a water content of from 5 to 20% by weight, preferably from 7 to 19% by weight, more preferably from 8 to 18% by weight.

When the aqueous glycolic acid solution (A) has a water content of less than 5% by weight, problems arise not only in that the purity of the final glycolic acid crystals is lowered, but also in that the aqueous glycolic acid solution (A) per se or the glycolic acid crystals-containing slurry which is obtained after the deposition of glycolic acid crystals from the aqueous glycolic acid solution (A) becomes too viscous, such that the handling property thereof is lowered and that it becomes difficult to separate the deposited glycolic acid crystals from the aqueous glycolic acid solution (A). On the other hand, when the aqueous glycolic acid solution (A) has a water content of more than 20% by weight, the purity of the final glycolic acid crystals is lowered.

In the present invention, the water content of the aqueous glycolic acid solution (A) can be measured by means of a conventional water content measuring apparatus.

Next, explanation is made with respect to the above-mentioned characteristic (b).

As mentioned above, the aqueous glycolic acid solution (A) contains monomeric glycolic acid and a glycolic acid condensation product. In the present invention, it is necessary that the aqueous glycolic acid solution (A) have a calculated monomeric glycolic acid weight ratio of from 0.60 to 1.00. The calculated monomeric glycolic acid weight ratio is defined as a ratio of the total weight of the monomeric glycolic acid and the glycolic acid condensation product to the weight of the aqueous solution (A), wherein the weight of the glycolic acid condensation product is expressed in terms of the weight of component monomeric glycolic acid of the glycolic acid condensation product. The calculated monomeric glycolic acid weight ratio is preferably from 0.70 to 0.95, more preferably from 0.75 to 0.93.

When the aqueous glycolic acid solution (A) has a calculated monomeric glycolic acid weight ratio of less than 0.60, the yield of the final glycolic acid crystals becomes disadvantageously low. On the other hand, when the aqueous glycolic acid solution (A) has a calculated monomeric glycolic acid weight ratio of more than 1.00, problems arise not only in that the purity of the final glycolic acid crystals is lowered, but also in that the aqueous glycolic acid solution or the glycolic acid crystals-containing slurry which is obtained after the deposition of glycolic acid crystals from the aqueous glycolic acid solution becomes too viscous, such that the handling property thereof is lowered and it becomes difficult to separate the deposited glycolic acid crystals from the aqueous glycolic acid solution.

Next, explanation is made with respect to the above-mentioned characteristic (c).

In the present invention, the aqueous glycolic acid solution (A) has a monomeric glycolic acid content of from 20 to 57% by weight, preferably from 35 to 56% by weight, more preferably from 40 to 55% by weight.

When the aqueous glycolic acid solution (A) has a monomeric glycolic acid content of less than 20% by weight, the yield of the final glycolic acid crystals obtained therefrom becomes disadvantageously low. On the other hand, when the aqueous glycolic acid solution (A) has a monomeric glycolic acid content of more than 57% by weight, the purity of the final glycolic acid crystals is lowered.

The monomeric glycolic acid content of an aqueous glycolic acid solution (A) can be determined as follows. An aqueous glycolic acid solution (A) is diluted with dehydrated pyridine, followed by silylation, to thereby obtain a sample solution. The obtained sample solution is analyzed by gas chromatography so as to determine the content of the silylated product of monomeric glycolic acid in the sample solution. From the found value of the content of the silylated product of monomeric glycolic acid, the weight of monomeric glycolic acid contained in the sample solution is calculated. The monomeric glycolic acid content of the aqueous glycolic acid solution (A) is expressed in terms of % by weight of monomeric glycolic acid contained in the sample solution, based on the weight of the aqueous glycolic acid solution (A).

As mentioned above, the aqueous glycolic acid solution (A) may contain one or more impurities. However, it is preferred that the aqueous glycolic acid solution (A) has an impurity content (defined above) of not more than 28% by weight, more advantageously not more than 23% by weight, still more advantageously not more than 20% by weight.

Specific examples of impurities include carboxylic acids, such as formic acid, acetic acid, propionic acid, butanoic acid, pentanoic acid, hexanoic acid and methoxyacetic acid; polycarboxylic acids, such as oxalic acid, malonic acid, gultaric acid, succinic acid, adipic acid, pimelic acid, suberic acid, azelaic acid, sebacic acid, undecanedioic acid, dodecanedioic acid, fumaric acid, maleic acid, diglycolic acid, 1,4-cyclohexanedicarboxylic acid, 1,3,4-butanetricarboxylic acid, 1,3,6-hexanetricarboxylic acid, phthalic acid, isophthalic acid, terephthalic acid, propanetricarboxylic acid, trimellitic acid, pyromellitic acid and ethylenediaminetetraacetic acid; monohydric alcohols, such as methanol, ethanol, 1-propanol, 2-propanol, 1-butanol, 2-butanol, 2-methyl-1-propanol, 2-methyl-2-propanol, 1-pentanol and 1-hexanol; polyols, such as ethylene glycol, 1,3-propanediol, 1,2-propanediol, 1,4-butanediol, 2,3-butanediol, 1,5-pentanediol, 1,6-hexanediol, 1,7-heptanediol, 1,8-octanediol, 1,9-nonanediol, 1,10-decanediol, 1,12-dodecanediol, 1,4-cyclohexanediol, 1,2-cyclohexanediol, 1,3-cyclohexanediol, neopentyl glycol, bisphenol A, diethylene glycol, triethylene glycol, tetraethylene glycol, oligomers of formaldehyde, glycerin and butane-1,2,3-triol; polysaccharides, such as starch, glucose, cellulose, hemicellulose, xylan, xylose, xylitol, pentaerythritol, chitin, chitosan, dextrin, dextran, carboxymethyl cellulose, amylopectin and glycogen; hydroxycarboxylic acids, such as lactic acid, 2-hydroxypentanoic acid, 2-hydroxyhexanoic acid, 2-hydroxyheptanoic acid, 2-hydroxyoctanoic acid, 2-hydroxy-2-methylpropanoic acid, 2-hydroxy-2-methylbutanoic acid, 2-hydroxy-2-ethylbutanoic acid, 2-hydroxy-2-methylpentanoic acid, 2-hydroxy-2-ethylpentanoic acid, 2-hydroxy-2-propylpentanoic acid, 2-hydroxy-2-butylpentanoic acid, 3-hydroxypropanoic acid, 3-hydroxybutanoic acid, 3-hydroxypentanoic acid, 3-hydroxyhexanoic acid, 3-hydroxyheptanoic acid, 3-hydroxyoctanoic acid, 3-hydroxy-3-methylbutanoic acid, 3-hydroxy-3-methylpentanoic acid, 3-hydroxy-3-ethylpentanoic acid, 4-hydroxybutanoic acid, 4-hydroxypentanoic acid, 4-hydroxyhexanoic acid, 4-hydroxyheptanoic acid, 4-hydroxyoctanoic acid, 4-hydroxy-4-methylpentanoic acid, 5-hydroxypentanoic acid, hydroxybenzoic acid, glyceric acid, diglyceric acid, tartaric acid, malic acid and citric acid; ammonia and monoamines, such methylamine, ethylamine and aniline; polyamines, such as hydrazine, methylhydrazine, monomethylenediamine, dimethylenediamine, trimethylenediamine, tetramethylenediamine, pentamethylenediamine, hexamethylenediamine, heptamethylenediamine, octamethylenediamine, nonamethylenediamine, decamethylenediamine, undecamethylenediamine and dodecamethylenediamine; amino acids, such as glycine, (+)-alanine, β-alanine, (−)-asparagine, (+)-aspartic acid, (−)-cysteine, (+)-glutamic acid, (+)-glutamine, (−)-hydroxylysine, (−)-leucine, (+)-isoleucine, (+)-lysine, (−)-methionine, (−)-serine, (−)-threonine, (+)-valine, aminobutyric acid, azaserine, arginine and ethinine; aldehydes, such as formaldehyde and acetaldehyde; and ketones, such as acetone and methyl ethyl ketone.

Further specific examples of impurities include elements belonging to Group 1 of the Periodic Table, such as lithium, sodium, potassium, rubidium, cesium and francium; elements belonging to Groups 2 to 12 of the Periodic Table; elements belonging to Group 13 of the Periodic Table, such as aluminum, gallium, indium and thallium; elements belonging to Group 14 of the Periodic Table, such as tin, lead and germanium; elements belonging to Group 15 of the Periodic Table, such as antimony; elements belonging to Group 16 of the Periodic Table, such as tellurium; and ions of the above-mentioned elements.

Still further examples of impurities include compounds, each containing one of the above-mentioned elements. More specific examples of such impurities include compounds, each independently being a salt of:

a metal ion selected from the group consisting of a lithium ion, a sodium ion, a potassium ion, a barium ion, a magnesium ion, a calcium ion, a chromium ion, a zinc ion, a lead ion, a nickel ion, a manganese ion, an iron ion, a niobium ion, a vanadium ion, a copper ion, a titanium ion, an aluminum ion, a lanthanum ion, a cerium ion, a strontium ion, a cobalt ion, a tungsten ion, a zirconium ion and a molybdenum ion, with an anion of a carboxyl group-containing compound, such as mentioned above (e.g., a monocarboxylic acid, a polycarboxylic acid, a hydroxycaroxylic acid or glycolic acid).

Still further examples of impurities include compounds containing at least two elements selected from the group consisting of elements belonging to Group 1 of the Periodic Table (e.g., lithium, sodium, potassium, rubidium, cesium and francium) and elements belonging to Groups 2 to 17 of the Periodic Table. More specific examples of such impurities include compounds, each independently being a salt of:

at least two metal ions selected from the group consisting of a lithium ion, a sodium ion, a potassium ion, a barium ion, a magnesium ion, a calcium ion, a chromium ion, a zinc ion, a lead ion, a nickel ion, a manganese ion, an iron ion, a niobium ion, a vanadium ion, a copper ion, a titanium ion, an aluminum ion, a lanthanum ion, a cerium ion and a strontium ion, with an anion selected from the group consisting of a fluoride ion, a chloride ion, a bromide ion, an iodide ion, a sulfate ion, a sulfite ion, a nitrate ion, a nitrite ion, a perchlorate ion, a phosphate ion, phosphate ion and borate ion.

In the aqueous glycolic acid solution (A), each of the compounds exemplified above as impurities may be present in the form of a self-condensation product or a condensation product of at least two different compounds. Further, each of these compounds may be present in the form of a condensation product thereof with glycolic acid.

The above-mentioned impurities may be compounds (such as diglycolic acid and lactic acid) by-produced during the production of the aqueous glycolic acid solution (A), compounds (such as sodium chloride) derived from the reagents used for synthesizing glycolic acid, or ions (such as a nickel ion, a chromium ion and a titanium ion) dissolved out from the apparatus used for the production of the aqueous glycolic acid solution (A).

Hereinbelow, explanation is made with respect to the method for producing an aqueous glycolic acid solution (A).

With respect to the method for producing an aqueous glycolic acid solution (A), there is no particular limitation, and any of the conventional methods can be used. For example, the aqueous glycolic acid solution (A) can be produced by a method comprising:

(1-i) producing an aqueous glycolic acid solution by a conventional method; and (1-ii) adjusting the water content, calculated monomeric glycolic acid weight ratio and monomeric glycolic acid content of the aqueous glycolic acid solution produced in step (1-i), to thereby obtain an aqueous glycolic acid solution (A).

With respect to step (1-i) above, explanation is made below.

Examples of conventional methods for producing an aqueous glycolic acid solution include chemical synthesis methods and fermentation methods using an enzyme, an yeast, a microbe and the like. In general, when glycolic acid is produced by any one of these methods, a compound having a carboxyl group and/or a hydroxyl group is by-produced during the production thereof.

Examples of the above-mentioned chemical synthesis methods include:

(a) a method in which glycolic acid is produced from formaldehyde, carbon monoxide and water in the presence of an acid catalyst (see, for example, Examined Japanese Patent Application Publication No. Sho 53-44454, and U.S. Pat. Nos. 2,037,654, 2,152,852 and 2,153,064);

(b) a method in which chloroacetic acid is subjected to saponification (see, for example, Unexamined Japanese Patent Application Laid-Open Specification No. Sho 62-77349);

(c) a method in which glyoxal is subjected to Cannizzaro reaction in the presence of a strong alkali to obtain a glycolic acid salt, followed by addition of an acid to thereby liberate glycolic acid from the salt (see, for example, Homolka, Chem. Ber., Vol. 54 (1921), p. 1395, and Salomaa Acta Chem. Scand., Vol. 10 (1956), p. 311);

(d) a method in which ethylene glycol is used as a raw material, and one of the hydroxyl group-containing terminals of the ethylene glycol is selectively converted into a carboxyl group (see, for example, Japanese Patent Application Publication No. 60-10016);

(e) a method in which glycolonitrile as a raw material is subjected to hydrolysis (see, for example, U.S. Pat. No. 4,054,601); and (f) a method in which oxalic acid is subjected to reduction (see, for example, P. Sevcik, Chemicke Zvesti, Vol. 27(3) (1973), p. 306).

In each of the above-mentioned methods (a) to (f), glycolic acid is obtained in the form of an aqueous solution thereof. Further, the reactions in the methods (d) and (e) can also be performed by the fermentation method as mentioned above. For example, the reactions in the methods (d) and (e) can be performed by the fermentation methods described in Unexamined Japanese Patent Application Laid-Open Specification Nos. Hei 10-174593 and Hei 9-28390.

The aqueous glycolic acid solutions obtained by the above-mentioned methods are commercially available, and such commercially available aqueous glycolic acid solutions can be used in the present invention. From the viewpoint of availability, it is preferred to use an aqueous glycolic acid solution which is produced by the above-mentioned method (a) or (b), and it is more preferred to use an aqueous glycolic acid solution produced by the above-mentioned method (a). The aqueous glycolic acid solutions obtained by the above-mentioned methods may be used individually or in combination.

When the aqueous glycolic acid solution contains an insoluble impurity (e.g., dust), it is preferred to remove such an insoluble impurity. The insoluble impurity may be removed by any conventional methods. Examples of conventional methods for removing an insoluble impurity include filtration, sedimentation, centrifugal separation and floatation. These methods may be used individually or in combination. Specific examples of filtration methods include constant-pressure filtration, constant-rate filtration, variable-pressure and variable-rate filtration, two or more dimensional filtration, clarifying filtration and filtration using a filter medium. These filtration methods may be used individually or in combination. Further, these filtration methods may be performed in a batchwise manner or in a continuous manner.

With respect to step (1-ii) above, explanation is made below.

In step (1-ii), the water content, calculated monomeric glycolic acid weight ratio and monomeric glycolic acid content of the aqueous glycolic acid solution produced in step (1-i) are adjusted to thereby obtain an aqueous glycolic acid solution (A). With respect to the method for adjusting the above-mentioned characteristics of the aqueous glycolic acid solution obtained in step (1-i), there is no particular limitation.

For example, when the aqueous glycolic acid solution obtained in step (1-i) has a calculated monomeric glycolic acid weight ratio (defined in characteristic (b)) and/or a monomeric glycolic acid content (defined in characteristic (c)) which are/is higher than its or their respective upper limits, the aqueous glycolic acid solution obtained in step (1-i) may be diluted with water, and optionally subjected to heat treatment under reduced pressure, atmospheric pressure or superatmospheric pressure, thereby obtaining an aqueous glycolic acid solution (A). The heat treatment is generally performed at 55 to 250° C., preferably at 70 to 200° C., more preferably at 80 to 170° C. Further, the heat treatment is generally performed under a pressure of from 101 kPa (atmospheric pressure) to 5,000 kPa, preferably from 101 kPa to 1,600 kPa, more preferably from 101 kPa to 790 kPa. An appropriate heat treatment time varies depending on the heat treatment temperature, the heat treatment pressure, the composition of the aqueous glycolic acid solution used, the amount of water used for diluting the aqueous glycolic acid solution, the desired values of the water content, calculated monomeric glycolic acid weight ratio and monomeric glycolic acid content of the aqueous glycolic acid solution (A) to be obtained. However, from the viewpoint of the hydrolysis rate of the glycolic acid condensation product contained in the aqueous glycolic acid solution, the heat treatment time can be appropriately selected within the range of from 1 second to 50 hours.

On the other hand, when the aqueous glycolic acid solution obtained in step (1-i) has a calculated monomeric glycolic acid weight ratio (defined in characteristic (b)) and/or a monomeric glycolic acid content (defined in characteristic (c)) which are/is lower than its or their respective lower limits, the aqueous glycolic acid solution obtained in step (1-i) may be subjected to dehydration/concentration under reduced pressure, atmospheric pressure or superatmospheric pressure, thereby obtaining an aqueous glycolic acid solution (A). The dehydration/concentration is generally performed at 55 to 250° C., preferably from 70 to 200° C., more preferably from 80 to 170° C. Further, the dehydration/concentration is generally performed under a pressure of from 0.001 to 4,000 kPa, preferably from 0.1 to 1,600 kPa, more preferably from 0.5 to 790 kPa. An appropriate dehydration/concentration time varies depending on the type of the apparatus used for dehydration/concentration, the dehydration/concentration temperature, the dehydration/concentration pressure, the composition of the aqueous glycolic acid solution used, the desired values of the water content, calculated monomeric glycolic acid weight ratio and monomeric glycolic acid content of the aqueous glycolic acid solution (A) to be obtained. However, from the viewpoint of the rate of withdrawal of water from apparatus used for dehydration/concentration and condensation rate of the monomeric glycolic acid in the aqueous glycolic acid solution, the dehydration/concentration time is appropriately selected within the range of from 1 second to 50 hours.

Next, explanation is made with respect to step (2) of the method of the present invention. In step (2), glycolic acid crystals are deposited from the aqueous glycolic acid solution (A) produced in step (1) above. With respect to the method for depositing glycolic acid crystals, there is no particular limitation, and any of the conventional methods can be used. For example, the deposition of glycolic acid crystals can be performed by cooling the aqueous glycolic acid solution (A) while allowing the solution (A) to stand still or while stirring. The deposition of glycolic acid crystals may be performed in a batchwise manner or in a continuous manner. Alternatively, the deposition of glycolic acid crystals may be performed in a manner wherein a batchwise operation and a continuous operation are used in combination.

With respect to a crystallizer used in step (2), there is no particular limitation and any of the conventional crystallizers can be used. Examples of conventional crystallizers include an agitation-type batch crystallizer, a single-vessel vacuum cooling crystallizer, a Swenson-Walker crystallizer, a Calandria type apparatus, a ring element type apparatus, a Crystal-Oslo type crystallizer, a D.T.B. (draft tube baffle) crystallizer, a D.P. (double propeller) crystallizer, a two-step granulation D.P. crystallizer, a turbulence crystallizer, a reverse cone type crystallizer, a pulse-column crystallizer, an air blow crystallizer, a rotary drum crystallizer, a spray evaporator/crystallizer (which utilizes the heat of vaporization of a coolant), a wetted wall crystallizer, a cooling disc crystallizer, a vertical multistage column crystallizer, a pressure crystallizer and the like, which are described at pages 75 to 122 of "Bessatsu Kagaku Kougyo 32-5 Kagaku souchi sekkei•sousa siriizu No. 3, Kaitei Shouseki (Separate volume of Chemical Engineering 32-5, Design and Operation of Chemical Devices, No. 3, Crystallization (revised edition))" published by Kagaku Kougyosha, Japan, in 1988. In addition, it is also possible to use a vertical, horizontal or inclined vessel or column which is not equipped with an agitator. The above-mentioned crystallizers can be used individually or in combination.

During the use of the above-mentioned crystallizers, if necessary, the aqueous glycolic acid solution (A) may be heated through the heat transfer surface of the crystallizer, or may be cooled by evaporation cooling utilizing latent heat or by cooling through the heat transfer surface of the crystallizer.

Hereinbelow, explanations are made on the above-mentioned crystallizers.

An agitation-type batch crystallizer is an apparatus equipped with an agitation blade and a coil or jacket for passing therethrough a temperature control medium. In this crystallizer, crystals are deposited by agitating a solution at appropriate temperatures.

A single-vessel vacuum cooling crystallizer is an apparatus equipped with an agitation blade at the bottom of the vessel. In this crystallizer, crystals are deposited by reducing the pressure of the vessel to thereby cool a solution contained therein by latent heat of evaporation.

A Swenson-Walker crystallizer is an apparatus having a trough-shaped vessel, wherein the vessel is provided with a jacket for passing therethrough a temperature control medium and contains a helical agitation blade therein. In this crystallizer, the temperature of a solution in the vessel is controlled through the heat transfer surface of the vessel, and crystals are deposited by agitating the solution at appropriate temperatures.

A Calandria type apparatus is a crystallizer having accommodated therein an agitator and a Calandria type heat exchanger. The temperature of a solution fed to the crystallizer is controlled by means of the heat exchanger to thereby deposit crystals from the solution.

A ring element type apparatus is a crystallizer having accommodated therein an agitator and a ring element type heat exchanger. The temperature of a solution fed to the crystallizer is controlled by means of the heat exchanger to thereby deposit crystals from the solution.

A Crystal-Oslo type crystallizer is a classifying fluidized-bed type crystallizer comprising an evaporation zone and a crystal growth zone, wherein a solution obtained in the evaporation zone is fed through a down-flow pipe to the crystal growth zone, to thereby deposit crystals from the solution.

A D.T.B. (draft tube baffle) crystallizer is an apparatus having accommodated therein a draft tube and an agitation blade. A solution having its temperature appropriately adjusted is fed to the inside of the crystallizer, and crystals are grown or deposited inside the crystallizer while circulating the solution to thereby classify the crystals.

A D.P. (double propeller) crystallizer is a modified form of the D.T.B. crystallizer, wherein an additional agitation blade is attached to the outer surface of the draft tube so that a solution is satisfactorily circulated in the system even at a low agitation rate.

A two-step granulation D.P. crystallizer is a modified form of the above-mentioned D.P. crystallizer.

A turbulence crystallizer is a modified form of the above-mentioned D.T.B. crystallizer. In this crystallizer, a solution is fed to the bottom portion of the crystallizer and mixed with a primary circulating fluid in the crystallizer while flowing the solution upwardly to an evaporation zone of the crystallizer. Then, the solution is circulated in a tube while adiabatically cooling the solution to thereby grow or deposit the crystals.

A reverse cone type crystallizer is a modified form of the above-mentioned Crystal-Oslo crystallizer. In this crystallizer, the distribution of the voids formed between the crystal particles is narrowed so as to increase the average suspension density of crystals inside the crystallizer.

A pulse-column crystallizer is a crystallizer having accommodated therein a cooling column. In this crystallizer, pulse is used to prevent scales from adhering to the cooling column.

An air blow crystallizer is an apparatus wherein, instead of using an agitator or a circulation pump, air is blown into the crystallization vessel to thereby circulate the solution in the vessel.

A rotary drum crystallizer is an apparatus comprising a vessel and a rotary drum. A temperature control medium is continuously fed into the rotary drum to control the temperature of a solution adhering to the heat transfer surface of the rotary drum, thereby depositing crystals on the heat transfer surface.

A spray evaporator/crystallizer is an apparatus in which a coolant, such as a petroleum hydrocarbon, is sprayed into a solution and the solution is cooled by the heat of vaporization of the coolant, thereby depositing crystals from the solution.

A wetted wall crystallizer is an apparatus comprising a horizontal tube into which a solution is sprayed and a temperature-controlled air is blown from a blower to thereby deposit crystals.

A cooling disc crystallizer is an apparatus comprising a horizontal vessel, in which the inside of the vessel is divided into a plurality of unit compartments. In this crystallizer, crystals are deposited by continuously and sequentially passing a solution or slurry through the unit compartments.

A vertical multistage column crystallizer is vertical version of the cooling disc crystallizer. That is, a vertical multistage column crystallizer comprises a vertical vessel, in which the inside of the vertical vessel is divided into a plurality of unit compartments. In this crystallizer, crystals are deposited by continuously and sequentially passing a solution or slurry through the unit compartments.

A pressure crystallizer is an apparatus in which a solution is adiabatically pressurized to change the solid-liquid state of the solution, thereby depositing crystals from the solution.

An appropriate temperature for depositing glycolic acid crystals varies depending on the composition of the aqueous glycolic acid solution (A), but it is preferred that the deposition of glycolic acid crystals from the aqueous glycolic acid solution (A) is performed at a temperature in the range of from −30 to 50° C., more preferably from −15 to 40° C., most preferably from −10 to 30° C. When the temperature is below −30° C., there is a danger that a supercooled solution may be solidified by freezing or coagulation. On the other hand, when the temperature exceeds 50° C., the crystallization proceeds slowly and the crystallization yield is likely to become disadvantageously low.

The temperature for depositing crystals may fluctuate during the crystal deposition operation. Therefore, when crystal deposition is performed at a temperature in the range of from −30 to 50° C., the temperature may be gradually elevated or lowered within the range of from −30 to 50° C. Further, a cycle of the elevation and subsequent lowering of the temperature (or vice versa) within the above-mentioned temperature range can be repeated during the crystal deposition operation.

There is no particular limitation with respect to the atmosphere used for depositing glycolic acid crystals. For example, crystal deposition may be performed in air or under a stream of air, or may be performed in an inert gas (such as nitrogen, helium, neon, argon, krypton, xenon, carbon dioxide or a lower hydrocarbon) or under a stream of an inert gas. These gases can be used individually or in combination.

With respect to the time for performing the crystal deposition, there is no particular limitation as long as the time is sufficient for the deposition of glycolic acid crystals to proceed satisfactorily. In general, the crystal deposition is performed for 1 minute to 50 hours, preferably 2 minutes to 10 hours, most preferably 3 minutes to 3 hours.

The deposition of glycolic acid crystals from the aqueous glycolic acid solution (A) is preferably performed in the presence of glycolic acid crystals as seed crystals. The crystallization of glycolic acid can be induced by the presence of seed crystals.

It is preferred that the purity of glycolic acid crystals used as seed crystals is as high as possible. The purity of the seed crystals, in terms of the above-mentioned purity, is generally 99% by weight or more, preferably 99.5% by weight or more, more preferably 99.8% by weight or more.

With respect to the amount of the seed crystals, there is no particular limitation as long as the seed crystals induce crystallization. The amount of the seed crystals used is generally from 0.001 to 100 g, preferably from 0.01 to 50 g, more preferably from 0.1 to 20 g, per kg of the aqueous glycolic acid solution (A).

In step (2), glycolic acid crystals are deposited in the aqueous solution, thereby forming a slurry comprising the glycolic acid crystals dispersed in an aqueous solution.

Next, explanation is made with respect to step (3) of the method of the present invention. In step (3), the deposited glycolic acid crystals are separated from aqueous glycolic acid solution (A), that is, the above-mentioned slurry is subjected to a solid-liquid separation. The solid-liquid separation may be performed in a continuous manner or a batchwise manner. Alternatively, the solid-liquid separation may be performed in a manner wherein a batchwise operation and a continuous operation are used in combination.

With respect to the method for performing the solid-liquid separation, there is no particular limitation, and any of the conventional methods can be used. Examples of conventional methods for solid-liquid separation include reduced pressure (vacuum) filtration, pressure filtration, centrifugal filtration and separation by precipitation. The above-mentioned filtration methods may be performed individually or in combination, and may be performed in combination with dehydration under a stream of air and/or compression.

When glycolic acid crystals separated in step (3) contain moisture, high purity glycolic acid crystals can be obtained by drying the separated glycolic acid crystals to thereby remove moisture completely from the glycolic acid crystals. However, even when glycolic acid crystals contain moisture, such glycolic acid crystals can be used as a raw material for producing a high molecular weight resin.

In the present invention, the separated glycolic acid crystals may be subjected to drying. There is no particular limitation with respect to the method for drying the glycolic acid crystals, but the drying is generally performed at a temperature below the melting point of glycolic acid and under reduced pressure, atmospheric pressure or superatmospheric pressure. Alternatively, the drying of the crystals can be performed under a flow of gas. These methods can be performed individually or in combination. There is no particular limitation with respect to the atmosphere used for drying the glycolic acid crystals. For example, drying can be performed in an atmosphere of air or an inert gas, such as nitrogen, helium, neon, argon, krypton, xenon, carbon dioxide or a lower hydrocarbon. These gases can be used individually or in combination.

High purity glycolic acid crystals can be obtained by the above-mentioned method of the present invention. However, for further improving the purity of the glycolic acid crystals, it is preferred that, after step (3) and before drying the crystals, residual products, such as a mother liquor, contained in a cake of glycolic acid crystals are completely removed with a washing liquid. Alternatively, the cake of glycolic acid crystals present in the slurry may be washed with a washing liquid so that washed crystals can be obtained by the solid-liquid separation in step (3). Further, the dried glycolic acid crystals obtained after step (3) and the subsequent drying operation may be washed with a washing liquid, followed by solid-liquid separation by the method described above in connection with step (3). The separated crystals can be dried again in the above-mentioned manner.

Examples of washing liquids include cold water having a temperature of higher than 0° C. and not higher than 5° C.; alcohols having 1 to 5 carbon atoms, such as methanol, ethanol, 1-propanol, 2-propanol, 1-butanol, 2-butanol, 2-methyl-1-propanol, 2-methyl-2-propanol and 1-pentanol; ketones, such as acetone, methyl ethyl ketone and methyl isobutyl ketone; and an aqueous glycolic acid solution. Of these, the aqueous glycolic acid solution is preferred from the viewpoint of safety, recyclability after the washing operation, and suppression of a lowering of the yield of the recovered crystals.

When an aqueous glycolic acid solution is used as a washing liquid, the method of the present invention further comprises, after step (3), the step of:

(4) washing the separated glycolic acid crystals with an aqueous glycolic acid solution (B).

Hereinbelow, explanation is made on the method comprising step (4).

It is preferred that the aqueous glycolic acid solution (B) contains monomeric glycolic acid and optionally a glycolic acid condensation product, and the aqueous glycolic acid solution (B) satisfies the following formulae (I) and (II):

$$0.0055 \times T + 0.3 \leq W \leq 0.0072 \times T + 0.8 \quad \text{(I)}$$

$$-5 \leq T \leq 70 \quad \text{(II)}$$

wherein:

W represents a calculated monomeric glycolic acid weight ratio of the aqueous solution (B), the calculated monomeric glycolic acid weight ratio being defined as a ratio of the total weight of the monomeric glycolic acid and the glycolic acid condensation product to the weight of the aqueous solution (B), wherein the weight of the glycolic acid condensation product is expressed in terms of the weight of component monomeric glycolic acid of the glycolic acid condensation product, and T represents the temperature (° C.) of the aqueous solution (B).

When the calculated monomeric glycolic acid weight ratio (W) of the aqueous glycolic acid solution (B) is less than $0.0055 \times T + 0.3$, the yield of the glycolic acid crystals is likely to become lowered. On the other hand, when the calculated monomeric glycolic acid weight ratio (W) of the aqueous glycolic acid solution (B) exceeds $0.0072 \times T + 0.8$, deposition of crystals is likely to occur during storage and/or transfer of the aqueous glycolic acid solution (B).

Temperature T is preferably in the range of from 0 to 65° C., more preferably from 25 to 60° C.

When temperature T is below −5° C., the effect of washing becomes unsatisfactory. On the other hand, when temperature T is above 70° C., the calculated monomeric glycolic acid weight ratio (W) of the aqueous glycolic acid solution (B) becomes markedly large, and a very large amount of the aqueous glycolic acid solution (B) becomes necessary for washing the crystals.

The temperature T and the calculated monomeric glycolic acid weight ratio (W) of the aqueous glycolic acid solution (B) may fluctuate during the washing operation as long as the aqueous glycolic acid solution (B) satisfies the above-mentioned formulae (I) and (II) at a predetermined point in time during the washing operation. Therefore, temperature T can be gradually elevated or lowered during the washing operation. Further, a cycle of the elevation and subsequent lowering of the temperature of the aqueous glycolic acid solution (B) (or vice versa) may be repeated during the washing operation.

It is preferred that the amount of impurities contained in the aqueous glycolic acid solution (B) is as small as possible. Specifically, as the aqueous glycolic acid solution (B), it is preferred to use an aqueous glycolic acid solution in which the ratio of the total weight of the monomeric glycolic acid and the glycolic acid condensation product to the total weight of the components, exclusive of water, of the aqueous glycolic acid solution (B) is high. More specifically, the above-mentioned ratio of the aqueous solution (B) is preferably 0.995 or more, more preferably 0.998 or more, still more preferably 0.999 or more. It is preferred that the above ratio is as high as possible.

The amount of the aqueous glycolic acid solution (B) used in the washing operation is generally 0.0001 to 4 liters, preferably 0.005 to 2.5 liters, more preferably 0.01 to 1.5 liters, per kg of the aqueous glycolic acid solution (A), wherein the amount of the aqueous glycolic acid solution (B) is measured at the temperature for performing the washing operation. When the aqueous glycolic acid solution (B) is portionwise added to the aqueous glycolic acid solution (A) or the glycolic acid crystals, the above-mentioned amount of the aqueous glycolic acid solution (B) is the total amount of the portions of the aqueous glycolic acid solution (B) used in the washing operation.

In step (4), there is no particular limitation with respect to the method for washing the crystals, and the residual products can be removed by any of the conventional washing methods. Examples of conventional washing methods include a displacement washing method in which a washing liquid is caused to permeate through a cake of glycolic acid crystals so as to displace the residual products (contained in the voids formed between the crystal particles) with the washing liquid, thereby removing the residual products; and a cake washing method in which a cake of glycolic acid crystals are dispersed into the washing liquid to thereby obtain a slurry and, then, the obtained slurry is subjected to a solid-liquid separation again. In addition, it is also possible to employ a method in which crystals are purified by utilizing the "sweating" phenomenon and the washing effect of the crystals (for example, a method which employs a K.C.P. continuous crystal purification apparatus (Kureha Crystal Purifier, manufactured and sold by Kureha Techno Eng. Co., Ltd., Japan) described at pages 99 to 100 of "Bessatsu Kagaku Kougyo 32-5 Kagaku souchi sekkei•sousa siriizu No. 3, Kaitei Shouseki (Additional volume of Chemical Engineering 32-5, Design and Operation of Chemical Devices, No. 3, Crystallization (revised edition))" published by Kagaku Kougyosha, Japan, in 1988). The above-mentioned methods may be performed individually or in combination.

The above-mentioned washing methods can be employed even when any of the above-mentioned washing liquids other than the aqueous glycolic acid solution (B) are used.

As mentioned above, the washing operation can be performed with respect to the slurry containing the cake of glycolic acid crystals prior to the solid-liquid separation. In this case, any of the above-mentioned washing liquids can be used as the washing liquid and the methods explained above in connection with step (4) can be used to wash the crystals contained in the slurry.

Further, the washing operation can be performed with respect to the glycolic acid crystals obtained after step (3) and the subsequent drying operation. In this case, any of the above-mentioned washing liquids can be used as the washing liquid, and the methods explained above in connection with step (4) for washing the cake can be used to wash the crystals.

When a washing liquid is used to remove the residual products, if desired, the washing operation can be repeated several times. In such a case, it is preferred that the washing operation is performed in combination with the solid-liquid separation.

When an aqueous glycolic acid solution is used as the above-mentioned washing liquid, for the purpose of effective utilization of glycolic acid, it is preferred that a part or whole of the washing liquid recovered by the solid-liquid separation performed after the washing operation is recycled as a raw material for producing the aqueous glycolic acid solution (A) or as a washing liquid.

Further, for the purpose of effective utilization of the glycolic acid, it is preferred that a part or whole of the mother liquor obtained after separating the glycolic acid crystals is recycled for use as a raw material for producing the aqueous glycolic acid solution (A).

There is no particular limitation with respect to the method for recycling the mother liquor. For example, the mother liquor as such or a concentrated product thereof may be recycled. Further, a part or whole of the mother liquor may be recycled after adding a fresh aqueous glycolic acid solution thereto.

For example, when the mother liquor satisfies all of the characteristics (a), (b) and (c) of the aqueous glycolic acid solution (A) used in the present invention, the mother liquor as such can be recycled as a raw material. Alternatively, before recycling, the mother liquor may be subjected to heating or dehydration/concentration under conditions wherein the characteristics (a), (b) and (c) of the mother liquor remain satisfied. If necessary, the mother liquor can be diluted with water before or after the heating, or after the dehydration/concentration. On the other hand, when the mother liquor does not satisfy at least one of the characteristics (a), (b) and (c) of the aqueous glycolic acid solution (A), before recycling the mother liquor, the characteristics of the mother liquor may be adjusted by the method described above in connection with step (1-ii) so that the mother liquor satisfies all of the characteristics (a), (b) and (c).

A part or whole of the mother liquor may be recycled after adding a fresh aqueous glycolic acid solution thereto. When a glycolic acid solution obtained by adding a fresh aqueous glycolic acid solution to the mother liquor satisfies all of the characteristics (a), (b) and (c) of the aqueous glycolic acid solution (A), the glycolic acid solution as such can be recycled as a raw material. Alternatively, before recycling, the glycolic acid solution can be subjected to heating or dehydration/concentration under conditions wherein the characteristics (a), (b) and (c) of the glycolic acid solution remain satisfied. If necessary, the glycolic acid solution can be diluted with water before or after the heating, or after the dehydration/concentration. On the other hand, when the glycolic acid solution obtained by adding a fresh aqueous glycolic acid solution to the mother liquor does not satisfy at least one of the characteristics (a), (b) and (c) of the aqueous glycolic acid solution (A), before recycling the glycolic acid solution, the characteristics of the glycolic acid solution may be adjusted by the method described above in connection with step (1-ii) so that the glycolic acid solution satisfies all of the characteristics (a), (b) and (c).

With respect to the material used for producing the apparatuses used in the step for producing the aqueous glycolic acid solution (A) and the above-mentioned steps (1) to (4), there is no particular limitation, and the material is generally selected from the group consisting of a glass, a stainless steel, a carbon steel, nickel, a hastelloy, titanium, chromium, zirconium, tantalum, other metal alloys, and ceramics. If desired, the surface of the apparatus may be treated by metal plating, lining, passivation or the like.

The high purity glycolic acid crystals obtained by the method of the present invention can be used not only as a component of cosmetics, hair dyes, shampoos, detergents (household detergents and industrial detergents), metal treating agents and agents for tanning leather, but also as a raw material for chemical synthetic products and resins (especially, high molecular weight resins).

For example, glycolide can be synthesized using the high purity glycolic acid crystals obtained by the method of the present invention. There is no particular limitation with respect to the method for synthesizing glycolide. As examples of such methods, there can be mentioned methods described in Unexamined Japanese Patent Application Laid-Open Specification Nos. 2000-119269 and 2002-114775.

Further, a glycolic acid homopolymer resin and a glycolic acid copolymer resin, each having a weight average molecular weight of 150,000 or more, can be produced using the high purity glycolic acid crystals obtained by the method of the present invention. There is no particular limitation with respect to the method for producing such a high molecular weight resin, and any of the conventional methods can be used. For example, as a method for producing a glycolic acid/lactic acid copolymer having a weight average molecular weight of 150,000 or more, there can be mentioned a method described in Unexamined Japanese Patent Application Laid-Open Specification No. 2002-293905.

Needless to say, the high purity glycolic acid crystals obtained by the method of the present invention can be used as a raw material for producing a glycolic acid homopolymer resin and a glycolic acid copolymer resin, each having a weight average molecular weight of less than 150,000. With respect to a method for producing such a low molecular weight resin, there is no particular limitation, and any of the conventional methods can be used.

In the present invention, the weight average molecular weight of a polymer can be determined by gel permeation chromatography (GPC).

Best Mode for Carrying Out the Invention

Hereinbelow, the present invention will be described in more detail with reference to the following Production Examples, Examples and Comparative Examples, which should not be construed as limiting the scope of the present invention.

In the following Production Examples, Examples and Comparative Examples, various measurements, analyses and calculations were performed by the following methods.

(1) Water Content of Aqueous Glycolic Acid Solution

The water content of an aqueous glycolic acid solution was measured by means of a Karl Fischer moisture content meter (trade name: MOISTURE METER™ CA-05; manufactured and sold by MITSUBISHI CHEMICAL CORPORATION, Japan). Specifically, about 0.2 g of an aqueous glycolic acid solution was weighed and added to a Karl Fischer reagent (trade name: AQUAMICRON™ AKS; manufactured and sold by MITSUBISHI CHEMICAL CORPORATION, Japan) to obtain a mixture, and the water content of the aqueous glycolic acid solution was measured with respect to the obtained mixture by means of the Karl Fischer moisture content meter.

(2) Calculated Monomeric Glycolic Acid Weight Ratio and Impurity Content of Aqueous Glycolic Acid Solution About 5 g of an aqueous glycolic acid solution (hereinafter, referred to as "feedstock liquid") was weighed and fed into a 50 ml-volumetric flask together with 20 ml of an 8 N aqueous solution of sodium hydroxide, and the resultant aqueous solution was allowed to stand for 10 hours to thereby hydrolyze a glycolic acid condensation product contained in the aqueous solution. Subsequently, 12.5 ml of concentrated hydrochloric acid (35 to 37% HCl reagent, manufactured and sold by Wako Pure Chemical Industries Ltd., Japan) was fed into the 50 ml-volumetric flask to acidify the aqueous solution, followed by dilution with distilled water so as to obtain 50 ml of a sample solution. The obtained sample solution was analyzed by high performance liquid chromatography (HPLC) under the following conditions:

Columns: RSpak™ KC-811 (manufactured and sold by Showa Denko K.K., Japan) (two columns were connected in series);

Column temperature: 40° C.;

Eluent: 0.75% by weight aqueous solution of phosphoric acid;

Flowing rate of eluent: 1 ml/min; and

Detector: UV detector (detecting wavelength: 210 nm).

By HPLC, an HPLC chromatogram was obtained, which showed peaks ascribed to monomeric glycolic acid and an organic compound as an impurity (e.g., diglycolic acid), respectively, which were detected by the UV detector at 210 nm. With respect to the observed peaks, the peak area counts were measured.

Separately from the above, a calibration curve was obtained with respect to glycolic acid, which showed the relationship between the weight of monomeric glycolic acid and the peak area of monomeric glycolic acid. Then, using the calibration curve, the weight of monomeric glycolic acid contained in the sample solution was determined from the peak area counts for monomeric glycolic acid.

Further, separately from the above, a calibration curve was obtained with respect to the organic compound as an impurity, which showed the relationship between the weight of the organic compound and the peak area of the organic compound. Then, using the obtained calibration curve, the weight of the organic compound was determined from the peak area counts for the organic compound. The impurity content of an aqueous glycolic acid solution was expressed in terms of % by weight of the impurity contained in the sample solution, based on the weight of the feedstock liquid. When the sample solution contained two or more organic compounds as impurities, the content of the total of impurities was defined as the impurity content of the feedstock liquid.

In each of Examples 1 to 8 and Comparative Examples 1 to 6, the aqueous glycolic acid solution used therein contained substantially no inorganic substance as an impurity and, hence, there was no need for measuring the amount of an inorganic compound contained in the aqueous glycolic acid solution. However, in Example 9, the aqueous glycolic acid solution used therein contained sodium chloride as an inorganic impurity. Therefore, in Example 9, the amount of sodium chloride contained in the aqueous glycolic acid solution was determined by the methods described in items (3) to (5) below, and the content of the total of the impurity organic compound and sodium chloride was defined as the impurity content of the aqueous glycolic acid solution.

(3) Sodium Ion Content of Aqueous Glycolic Acid Solution

About 5 g of an aqueous glycolic acid solution (hereinafter, referred to as "feedstock liquid") was weighed and fed into a 200 ml-volumetric flask. Then, the aqueous glycolic acid solution was diluted with distilled water to obtain 200 ml of a sample solution. The obtained sample solution was analyzed by ion chromatography (IC) under the following conditions:

Apparatus: 8020 series (trade name; manufactured and sold by Tosoh Corporation, Japan);

Column: TSKgel IC-Cation (trade name; manufactured and sold by Tosoh Corporation, Japan);

Column temperature: 40° C.;

Eluent: 2 mmol/l aqueous nitric acid solution;

Flow rate of eluent: 0.5 ml/min; and

Detector: conductivity meter CM-8020 (trade name; manufactured and sold by Tosoh Corporation, Japan).

By IC, an IC chromatogram was obtained, which showed a peak ascribed to a sodium ion detected by the conductivity meter. With respect to the observed peak, the peak area counts were measured.

Separately from the above, a calibration curve was obtained with respect to sodium ion, which showed the relationship between the weight of sodium ion and the peak area of sodium ion. Then, using the obtained calibration curve, the weight of sodium ion contained in the sample solution was determined from the peak area counts for sodium ion. The sodium ion content of the feedstock liquid was expressed in terms of % by weight of sodium ion contained in the sample solution, based on the weight of the feedstock liquid.

(4) Chloride Ion Content of Aqueous Glycolic Acid Solution

About 5 g of aqueous glycolic acid solution (hereinafter, referred to as "feedstock liquid") was weighed and fed into a 200 ml-volumetric flask. Then, the aqueous glycolic acid solution was diluted with distilled water to obtain 200 ml of a sample solution. The obtained sample solution was analyzed by ion chromatography (IC) under the following conditions:

Apparatus: 8020 series (trade name; manufactured and sold by Tosoh Corporation, Japan);

Column: TSKgel Super IC-Anion-PWXL PEEK (trade name; manufactured and sold by Tosoh Corporation, Japan);

Column temperature: 40° C.;

Eluent: TSKeluent IC-Anion-A (trade name; manufactured and sold by Tosoh Corporation, Japan);

Flow rate of eluent: 0.8 ml/min; and

Detector: conductivity meter CM-8020 (trade name; manufactured and sold by Tosoh Corporation, Japan).

By IC, an IC chromatogram was obtained, which showed a peak ascribed to a chloride ion detected by the conductivity meter. With respect to the observed peak, the peak area counts were measured.

Separately from the above, a calibration curve was obtained with respect to the chloride ion, which showed the relationship between the weight of the chloride ion and the peak area of the chloride ion. Then, using the obtained calibration curve, the weight of the chloride ion contained in the sample solution was determined from the peak area counts for the chloride ion. The chloride ion content of the feedstock liquid was expressed in terms of % by weight of the chloride ion contained in the sample solution, based on the weight of the feed-stock liquid.

(5) Sodium Chloride Content of Aqueous Glycolic Acid Solution

The sodium chloride content of an aqueous glycolic acid solution was calculated from the following formula:

(Sodium chloride content of aqueous glycolic acid solution (% by weight))=(sodium ion content of aqueous glycolic acid solution)+(chloride ion content of aqueous glycolic acid solution).

(6) Monomeric Glycolic Acid Content of Aqueous Glycolic Acid Solution

About 0.5 g of an aqueous glycolic acid solution (hereinafter, referred to as "feedstock liquid") was weighed and fed into a 50 ml-volumetric flask. Then, 0.1 g of n-dodecane was weighed and added to the aqueous glycolic acid solution as an internal standard. The resultant mixture in the volumetric flask was diluted with dehydrated pyridine to obtain 50 ml of a diluted solution. Then, 0.3 ml of the diluted solution was added to 1 ml of N,O-bis-trimethylsilylacetamide, and the resultant mixture was allowed to stand at room temperature for 1 hour, thereby obtaining a sample solution. The sample solution was analyzed by gas chromatography (GC) under the following conditions:

Column: DB-1 (trade name; manufactured and sold by J&W Scientific, U.S.A) (column length: 30 m, inner diameter: 0.25 mm, film thickness: 1 μm);

Carrier gas: helium;

Detector: hydrogen flame ionization detector (FID);

Injection temperature: 250° C.;

Detector temperature: 300° C.; and

Column temperature: first, the column temperature was elevated from 50 to 100° C. at a rate of 10° C./min and maintained at 100° C. for 10 minutes and, then, elevated to 250° C. at a rate of 10° C./min and maintained at 250° C. for 15 minutes.

By GC analysis, a GC chromatogram was obtained, which showed the peaks ascribed to the n-dodecane (internal standard) and a silylated product of the monomeric glycolic acid, respectively, and the peak area ratio of the n-dodecane to the silylated product of the monomeric glycolic acid was determined.

Separately from the above, a calibration curve was obtained with respect to the n-dodecane and the silylated product, which showed the relationship between the peak area ratio of the n-dodecane to the silylated product and the concentration ratio of the n-dodecane to the silylated product. Further, using the calibration curve, the concentration ratio of the n-dodecane contained in the sample solution to the silylated product contained in the sample solution was determined from the above-obtained peak area ratio. From the determined concentration ratio and the concentration of the n-dodecane in the sample solution, the concentration of the silylated product of the monomeric glycolic acid in the sample solution was determined. Further, from the obtained concentration of the silylated product, the weight of the monomeric glycolic acid contained in the sample solution was calculated. The monomeric glycolic acid content of the feedstock liquid was expressed in terms of % by weight of the monomeric glycolic acid contained in the sample solution, based on the weight of the feedstock liquid.

(7) Impurity Content and Purity of Glycolic Acid Crystals 4 g of dried glycolic acid crystals were weighed and fed into a 50 ml-volumetric flask together with 20 ml of an 8 N aqueous solution of sodium hydroxide, and the resultant mixture was subjected to hydrolysis for 5 hours. Subsequently, 12.5 ml of concentrated hydrochloric acid (35 to 37% HCl reagent, manufactured and sold by Wako Pure Chemical Industries Ltd., Japan) was fed into the 50 ml-volumetric flask to thereby acidify the aqueous solution, followed by dilution with distilled water so as to obtain 50 ml of a sample solution. The obtained sample solution was analyzed by high performance liquid chromatography (HPLC) under the following conditions:

Columns: RSpak™ KC-811 (manufactured and sold by Showa Denko K.K., Japan) (two columns were connected in series);

Measurement temperature: 40° C.;

Eluent: 0.75% by weight aqueous solution of phosphoric acid;

Flowing rate of eluent: 1 ml/min; and

Detector: UV detector (detecting wavelength: 210 nm).

By HPLC analysis, an HPLC chromatogram was obtained, which showed a peak ascribed to an organic compound as an impurity detected by the UV detector at 210 nm. With respect to the observed peak, the peak area counts were measured.

Separately from the above, a calibration curve was obtained with respect to the organic compound as an impurity, which showed the relationship between the weight of the organic compound and the peak area of the organic compound. Then, using the obtained calibration curve, the weight of the organic compound contained in the sample solution was determined from the peak area counts for the organic compound. The impurity content of the glycolic acid crystals was expressed in terms of % by weight of the impurity contained in the sample solution, based on the weight of the glycolic acid crystals. When the sample solution contained two or more organic compounds as impurities, the content of the total of the impurities was defined as the impurity content of the glycolic acid crystals.

In each of Examples 1 to 8 and Comparative Examples 1 to 6, the aqueous glycolic acid solution used therein contained substantially no inorganic substance as an impurity, so that there was no need for measuring the amount of inorganic compound contained in the glycolic acid crystals. However, in Example 9, the aqueous glycolic acid solution used therein contained sodium chloride as an inorganic impurity. Therefore, in Example 9, the amount of sodium chloride contained in the glycolic acid crystals was measured by the methods described in items (8) to (10) below, and the content of the total of the impurity organic compound and sodium chloride was defined as the impurity content of the glycolic acid crystals.

From the impurity content, the purity of the glycolic acid crystals was calculated by the following formula:

(Purity of glycolic acid crystals)=100−(impurity content of glycolic acid crystals)

As mentioned above, the amount of sodium chloride contained in the glycolic acid crystals was measured by the following methods described in items (8) to (10) below.

(8) Sodium Ion Content of Glycolic Acid Crystals

About 5 g of glycolic acid crystals was weighed and fed into a 50 ml-volumetric flask, and dissolved in distilled water to obtain an aqueous solution. Then, the aqueous solution was diluted with a further distilled water to thereby obtain 50 ml of a sample solution. The obtained sample solution was analyzed by ion chromatography (IC) under the following conditions:

Apparatus: 8020 series (trade name; manufactured and sold by Tosoh Corporation, Japan);

Column: TSKgel IC-Cation (trade name; manufactured and sold by Tosoh Corporation, Japan);

Column temperature: 40° C.;

Eluent: 2 mmol/l aqueous nitric acid solution;

Flow rate of eluent: 0.5 ml/min; and

Detector: conductivity meter CM-8020 (trade name; manufactured and sold by Tosoh Corporation, Japan).

By IC, an IC chromatogram was obtained, which showed a peak ascribed to a sodium ion detected by the conductivity meter. With respect to the observed peak, the peak area counts were measured.

Separately from the above, a calibration curve was obtained with respect to a sodium ion, which showed the relationship between the weight of the sodium ion and the peak area of the sodium ion. Then, using the obtained calibration curve, the weight of the sodium ion contained in the sample solution was determined from the peak area counts for the sodium ion contained in the sample solution. The sodium ion content of the glycolic acid crystals was expressed in terms of % by weight of the sodium ion contained in the sample solution, based on the weight of the glycolic acid crystals.

(9) Chloride Ion Content of Glycolic Acid Crystals

About 5 g of glycolic acid crystals were weighed and fed into a 50 ml-volumetric flask, followed by dilution with distilled water to thereby obtain 50 ml of a sample aqueous solution. The obtained sample aqueous solution was analyzed by ion chromatography (IC) under the following conditions:

Apparatus: 8020 series (trade name; manufactured and sold by Tosoh Corporation, Japan);

Column: TSKgel Super IC-Anion-PWXL PEEK (trade name; manufactured and sold by Tosoh Corporation, Japan);

Column temperature: 40° C.;

Eluent: TSKeluent IC-Anion-A (trade name; manufactured and sold by Tosoh Corporation, Japan);

Flow rate of eluent: 0.8 ml/min; and

Detector: conductivity meter CM-8020 (trade name; manufactured and sold by Tosoh Corporation, Japan).

By IC, an IC chromatogram was obtained, which showed a peak ascribed to a chloride ion detected by the conductivity meter. With respect to the observed peak, the peak area counts were measured.

Separately from the above, a calibration curve was obtained with respect to a chloride ion, which showed the relationship between the weight of the chloride ion and the peak area of the chloride ion. Then, using the obtained calibration curve, the weight of the chloride ion contained in the sample solution was determined from the peak area counts for the chloride ion contained in the sample solution. The chloride ion content of the glycolic acid crystals was expressed in terms of % by weight of chloride ion contained in the sample solution, based on the weight of the glycolic acid crystals.

(10) Sodium Chloride Content of Glycolic Acid Crystals

The sodium chloride content of glycolic acid crystals was calculated from the following formula:

(Sodium chloride content of glycolic acid crystals (% by weight))=(sodium ion content of glycolic acid crystals)+(chloride ion content of glycolic acid crystals).

(11) Yield of Obtained Glycolic Acid Crystals

The yield of the obtained glycolic crystals was calculated from the following formula:

Yield of glycolic acid crystals (wt %)=(weight of glycolic acid obtained)×100/(weight of aqueous glycolic acid solution)×(calculated monomeric glycolic acid weight ratio)

(12) Weight Average Molecular Weight of a Polymer

The weight average molecular weight of a polymer was measured by gel permeation chromatography (GPC).

Specifically, 80 mM sodium trifluoroacetate was dissolved in hexafluoroisopropanol to obtain an eluent. Then, using the obtained eluent, a polymer was flowed through a column (TSKgel™ G5000H-HR and TSKgel™ G3000H-HR (both manufactured and sold by Tosoh Corporation, Japan), which were connected in series) under conditions wherein the column temperature was 40° C. and the flow rate was 1 ml/min.

Separately from the above, a calibration curve was obtained as follows. With respect to the monodisperse standard polymethyl methacrylate (PMMA) samples having molecular weights of 1,577,000, 685,000, 333,000, 100,250, 62,600, 24,300, 12,700, 4,700 and 1680, respectively, the respective elution times were determined by refractive index (RI) detection. From the obtained values of the respective elution times, a calibration curve was obtained. Using the calibration curve, the weight average molecular weight of the polymer was determined from the elution time thereof.

(13) Melting Peak Temperature of a Polymer (Crystalline Prepolymer)

The melting peak temperature of a polymer (crystalline prepolymer) was measured in accordance with JIS K7121 by means of a differential scanning calorimeter (trade name: DSC-7; manufactured and sold by Perkin Elmer, Inc., U.S.A.). Specifically, a crystalline prepolymer was fed into the differential scanning calorimeter, and the internal temperature of the differential scanning calorimeter was elevated from −20° C. to 250° C. at a rate of 10° C./min, thereby obtaining a differential scanning calorimetry (DSC) chart (i.e., crystallization curve) with respect to the crystalline prepolymer. From the obtained DSC chart, the temperature at which the peak ascribed to the melting of the prepolymer was observed was defined as the melting peak temperature. Based on the melting peak temperature of the crystalline prepolymer, the temperature for the solid-phase polymerization of the crystalline prepolymer was determined.

PRODUCTION EXAMPLE 1 (PRODUCTION OF AN AQUEOUS GLYCOLIC ACID SOLUTION 1)

An aqueous glycolic acid solution 1 which satisfies the requirements concerning the aqueous glycolic acid solution (A) used in the present invention was prepared by adjusting the composition of a commercially available aqueous glycolic acid solution (GLYCOLIC ACID 70% SOLUTION-TECHNICAL, manufactured and sold by Du Pont, U.S.A.). The preparation of the aqueous glycolic acid solution 1 was performed as described below.

The above-mentioned commercially available aqueous glycolic acid solution had a water content of 31% by weight and a calculated monomeric glycolic acid weight ratio of 0.69. Further, the commercially available aqueous glycolic acid solution contained, as impurities, 1.2% by weight of diglycolic acid, 0.8% by weight of methoxyacetic acid and 0.4% by weight of formic acid.

The commercially available aqueous glycolic acid solution was subjected to dehydration/concentration under a stream of nitrogen gas under atmospheric pressure at 110 to 113° C. for 50 minutes, thereby obtaining an aqueous glycolic acid solution 1. The obtained aqueous glycolic acid solution 1 had a water content of 18% by weight, a calculated monomeric glycolic acid weight ratio of 0.83 and a monomeric glycolic acid content of 54.5% by weight. Further, the aqueous glycolic acid solution 1 contained, as impurities, 1.5% by weight of diglycolic acid, 0.8% by weight of methoxyacetic acid and 0.3% by weight of formic acid.

PRODUCTION EXAMPLE 2 (PRODUCTION OF AN AQUEOUS GLYCOLIC ACID SOLUTION 2)

An aqueous glycolic acid solution 2 which satisfies the requirements concerning the aqueous glycolic acid solution (A) used in the present invention was prepared by adjusting the composition of the commercially available aqueous glycolic acid solution used in Production Example 1. Specifically, the above-mentioned commercially available aqueous glycolic acid solution was subjected to dehydration/concentration under a stream of nitrogen gas under reduced pressure, namely under a pressure of 16 kPa, at 75° C. for 50 minutes, thereby obtaining an aqueous glycolic acid solution 2. The obtained aqueous glycolic acid solution 2 had a water content of 13% by weight, a calculated monomeric glycolic acid weight ratio of 0.91 and a monomeric glycolic acid content of 52% by weight. Further, the aqueous glycolic acid solution 2 contained, as impurities, 1.7% by weight of diglycolic acid, 1.0% by weight of methoxyacetic acid and 0.2% by weight of formic acid.

PRODUCTION EXAMPLE 3 (PRODUCTION OF AN AQUEOUS GLYCOLIC ACID SOLUTION 3)

An aqueous glycolic acid solution 3 which satisfies the requirements concerning the aqueous glycolic acid solution (A) used in the present invention was prepared by adjusting the composition of the commercially available aqueous glycolic acid solution used in Production Example 1. Specifically, the above-mentioned commercially available aqueous glycolic acid solution was subjected to dehydration/concentration under a stream of nitrogen gas under atmospheric pressure at 110 to 132° C. for 150 minutes, thereby obtaining an aqueous glycolic acid solution 3. The obtained aqueous glycolic acid solution 3 had a water content of 7% by weight, a calculated monomeric glycolic acid weight ratio of 1.0 and a monomeric glycolic acid content of 41% by weight. Further, the aqueous glycolic acid solution 3 contained, as impurities, 1.9% by weight of diglycolic acid, 1.1% by weight of methoxyacetic acid and 0.3% by weight of formic acid.

PRODUCTION EXAMPLE 4 (PRODUCTION OF AN AQUEOUS GLYCOLIC ACID SOLUTION 4)

A comparative aqueous glycolic acid solution 4 which does not satisfy the requirements concerning the aqueous glycolic acid solution (A) used in the present invention was prepared by adjusting the composition of the commercially available aqueous glycolic acid solution used in Production Example 1. Specifically, the above-mentioned commercially available aqueous glycolic acid solution was subjected to dehydration/concentration under a stream of nitrogen gas under atmospheric pressure at 110 to 135° C. for 160 minutes, thereby obtaining a comparative aqueous glycolic acid solution 4. The obtained comparative aqueous glycolic acid solution 4 had a water content of 3% by weight, a calculated monomeric glycolic acid weight ratio of 1.05 and a monomeric glycolic acid content of 35% by weight. Further, the comparative aqueous glycolic acid solution 4 contained, as impurities, 2.0% by weight of diglycolic acid, 1.1% by weight of methoxyacetic acid and 0.2% by weight of formic acid.

PRODUCTION EXAMPLE 5 (PRODUCTION OF AN AQUEOUS GLYCOLIC ACID SOLUTION 5)

An aqueous glycolic acid solution 5 which satisfies the requirements concerning the aqueous glycolic acid solution (A) used in the present invention was prepared by using commercially available glycolic acid crystals (guaranteed reagent manufactured and sold by TOKYO KASEI KOGYO CO., LTD., Japan). The preparation of the aqueous glycolic acid solution 5 was performed as described below.

450 g of distilled water, 990 g of glycolic acid crystals (guaranteed reagent manufactured and sold by TOKYO KASEI KOGYO CO., LTD., Japan) (which had been satisfactorily dried in vacuo at 35° C.), 11.6 g of chloroacetic acid (guaranteed reagent manufactured and sold by Wako Pure Chemical Industries, Ltd., Japan) and 198 g of sodium chloride (standard grade reagent for volumetric analysis, manufactured and sold by Wako Pure Chemical Industries, Ltd., Japan) were fed to a round-bottom flask which had an internal volume of 2 liters and was equipped with a stirrer, followed by stirring in air at a rate of 100 rpm at 27° C. for 5 hours, thereby obtaining an aqueous glycolic acid solution. The obtained aqueous glycolic acid solution had a water content of 28% by weight and a calculated monomeric glycolic acid weight ratio of 0.60. Further, the aqueous glycolic acid solution contained, as impurities, 0.7% by weight of chloroacetic acid and 12% by weight of sodium chloride. The aqueous glycolic acid solution was subjected to dehydration/concentration under a stream of nitrogen gas under atmospheric pressure at 113 to 125° C. for 150 minutes, to thereby deposit sodium chloride therefrom. Then, the deposited sodium chloride was removed from the resultant aqueous glycolic acid solution by pressure filtration under 0.3 MPa (in which nitrogen gas was used as a pressurizing medium) by means of a pressure filtration apparatus using a filter paper (3250, manufactured and sold by Azumi Filter Paper Co., Ltd., Japan), thereby obtaining an aqueous glycolic acid solution 5. The obtained aqueous glycolic acid solution 5 had a water content of 14% by weight, a calculated monomeric glycolic acid weight ratio of 0.91 and a monomeric glycolic acid content of 52% by weight. Further, the aqueous glycolic acid solution 5 contained, as impurities, 1.1% by weight of chloroacetic acid and 5% by weight of sodium chloride.

PRODUCTION EXAMPLE 6 (PREPARATION OF A WASHING SOLUTION 1)

An aqueous glycolic acid solution (hereinafter, referred to as "washing solution 1") which had a calculated monomeric glycolic acid weight ratio of 0.65 was prepared at a temperature of 5° C. by using glycolic acid crystals having a purity of 99.99% by weight or more and distilled water.

PRODUCTION EXAMPLE 7 (PREPARATION OF A WASHING SOLUTION 2)

An aqueous glycolic acid solution (hereinafter, referred to as "washing solution 2") which had a calculated monomeric glycolic acid weight ratio of 0.45 was prepared at a temperature of 5° C. by using glycolic acid crystals having a purity of 99.99% by weight or more and distilled water.

PRODUCTION EXAMPLE 8 (PREPARATION OF A WASHING SOLUTION 3)

An aqueous glycolic acid solution (hereinafter, referred to as "washing solution 3") which had a calculated monomeric glycolic acid weight ratio of 1.00 was prepared at a temperature of 55° C. by using glycolic acid crystals having a purity of 99.99% by weight or more and distilled water.

EXAMPLE 1

500 g of the aqueous glycolic acid solution 1 was fed to a flask which had an internal volume of 1 liter and was equipped with a stirrer and a thermometer. The aqueous glycolic acid solution 1 in the flask was cooled to 0° C., followed by addition of 0.5 g of glycolic acid crystals (purity: 99.99%) as seed crystals. From the resultant mixture were deposited crystals by stirring the mixture at a rate of 100 rpm for 15 minutes while maintaining the temperature of the mixture at 0° C., thereby obtaining a slurry containing deposited crystals.

The obtained slurry was subjected to vacuum filtration using a funnel (KIRIYAMA ROHTO SU-95, manufactured and sold by KIRIYAMA GLASS WORKS CO., LTD., Japan) and a filter paper (No. 5B, diameter: 95 mm; manufactured and sold by KIRIYAMA GLASS WORKS CO., LTD., Japan). After completion of a continuous discharge of the filtrate, the resultant residue was subjected to dehydration under a stream of air for 10 minutes, thereby recovering crystals. The vacuum filtration of the slurry and the separation of the crystals by dehydration under a stream of air were able to be performed efficiently.

The recovered crystals were washed with 100 ml of the washing solution 1 at 5° C., followed by vacuum filtration and dehydration under a stream of air which were performed in the same manner as mentioned above, to thereby remove impurities, such as a mother liquor contained in the recovered crystals. This series of the operations (i.e., the washing, the vacuum filtration and the dehydration under a stream of air) was repeated 4 times in total.

Subsequently, the resultant crystals were subjected to vacuum drying at 35° C. until the weight of the crystals became constant, thereby obtaining dried glycolic acid crystals.

The yield of the obtained, dried glycolic acid crystals was 27% by weight, and the purity of the dried glycolic acid crystals was 99.96% by weight.

EXAMPLE 2

Dried glycolic acid crystals were obtained in substantially the same manner as in Example 1, except that the washing solution 2 was used instead of the washing solution 1. The vacuum filtration of the slurry containing the deposited crystals and the separation of the crystals by dehydration under a stream of air were able to be performed efficiently.

The yield of the obtained, dried glycolic acid crystals was 20% by weight, and the purity of the dried glycolic acid crystals was 99.96% by weight.

EXAMPLE 3

Dried glycolic acid crystals were obtained in substantially the same manner as in Example 1, except that the aqueous glycolic acid solution 2 was used instead of the aqueous glycolic acid solution 1, and the time for the deposition of the glycolic acid crystals was changed to 2 hours. The vacuum filtration of the slurry containing the deposited crystals and the separation of the crystals by dehydration under a stream of air were able to be performed efficiently.

The yield of the obtained, dried glycolic acid crystals was 28% by weight, and the purity of the dried glycolic acid crystals was 99.97% by weight.

EXAMPLE 4

Dried glycolic acid crystals were obtained in substantially the same manner as in Example 3, except that the deposited crystals were subjected to pressure filtration under 0.3 MPa (in which air was used as a pressurizing medium) by means of a pressure filtration apparatus using a filter paper (3250, manufactured and sold by Azumi Filter Paper Co., Ltd., Japan), followed by dehydration of the resultant residue under a stream of air for 10 minutes (performed after completion of a continuous discharge of the filtrate), and that the recovered crystals were not washed. The pressure filtration of the slurry containing the deposited crystals and the separation of the crystals by dehydration under a stream of air were able to be performed efficiently.

The yield of the obtained, dried glycolic acid crystals was 28% by weight, and the purity of the dried glycolic acid crystals was 99.92% by weight.

EXAMPLE 5

Dried glycolic acid crystals were obtained in substantially the same manner as in Example 4, except that the aqueous glycolic acid solution 3 was used instead of the aqueous glycolic acid solution 2, that the temperature and time for the deposition of the glycolic acid crystals were changed to 10° C. and 45 minutes, respectively, and that nitrogen gas was used as a pressurizing medium in the pressure filtration. The pressure filtration of the slurry containing the deposited crystals and the separation of the crystals by dehydration under a stream of air were able to be performed efficiently.

The yield of the obtained, dried glycolic acid crystals was 23% by weight, and the purity of the dried glycolic acid crystals was 99.90% by weight.

COMPARATIVE EXAMPLE 1

A comparative aqueous glycolic acid solution 6 was produced as follows. 328 g of distilled water, 820 g of glycolic acid crystals (guaranteed reagent manufactured and sold by TOKYO KASEI KOGYO CO., LTD., Japan), 15.3 g of diglycolic acid crystals (guaranteed reagent manufactured and sold by Wako Pure Chemical Industries, Ltd., Japan), 8.2 g of methoxyacetic acid (reagent manufactured and sold by Wako Pure Chemical Industries, Ltd., Japan) and a 90% by weight aqueous solution of formic acid (guaranteed reagent manufactured and sold by Wako Pure Chemical Industries, Ltd., Japan) were fed to a round-bottom flask which had an internal volume of 2 liters and was equipped with a stirrer, followed by stirring at a rate of 50 rpm at 40° C. for 4 hours, thereby obtaining a comparative aqueous glycolic acid solution 6. The obtained comparative aqueous glycolic acid solution 6 had a water content of 31% by weight, a calculated monomeric glycolic acid weight ratio of 0.7 and a monomeric glycolic acid content of 59% by weight. Further, the comparative aqueous glycolic acid solution 6 contained, as impurities, 1.3% by weight of diglycolic acid, 0.7% by weight of methoxyacetic acid and 0.4% by weight of formic acid.

Then, dried glycolic acid crystals were produced in substantially the same manner as in Example 4, except that the above-obtained comparative aqueous glycolic acid solution 6 was used instead of the aqueous glycolic acid solution 2, and the temperature and time for the deposition of the glycolic acid crystals were changed to −18° C. and 1.5 hours, respectively. The pressure filtration of the slurry containing the deposited crystals and the separation of the crystals by dehydration under a stream of air were able to be performed efficiently.

The yield of the obtained, dried glycolic acid crystals was 20% by weight, and the purity of the dried glycolic acid crystals was as low as 99.47% by weight.

COMPARATIVE EXAMPLE 2

Dried glycolic acid crystals were obtained in substantially the same manner as in Example 1, except that the comparative aqueous glycolic acid solution 6 was used instead of the aqueous glycolic acid solution 1, and the temperature and time for the deposition of the glycolic acid crystals were changed to −18° C. and 1.5 hours, respectively. The vacuum filtration of the slurry containing the deposited crystals and the separation of the crystals by dehydration under a stream of air were able to be performed efficiently.

The yield of the obtained, dried glycolic acid crystals was 20% by weight, and the purity of the dried glycolic acid crystals was as low as 99.55% by weight.

COMPARATIVE EXAMPLE 3

Dried glycolic acid crystals were obtained in substantially the same manner as in Example 4, except that the comparative aqueous glycolic acid solution 4 was used instead of the aqueous glycolic acid solution 1, and the temperature and time for the deposition of the glycolic acid crystals were changed to 10° C. and 1 hour, respectively. The slurry containing the deposited crystals exhibited high viscosity. The pressure filtration of the slurry containing the deposited crystals and the separation of the crystals by dehydration under a stream of air were not able to be performed efficiently.

The yield of the obtained, dried glycolic acid crystals was 20% by weight, and the purity of the dried glycolic acid crystals was as low as 99.68% by weight.

COMPARATIVE EXAMPLE 4

The comparative aqueous glycolic acid solution 6 produced in Comparative Example 1 was subjected to dehydration/concentration under reduced pressure, namely under a pressure of from 4 to 5 kPa at 45° C. for 20 minutes, thereby obtaining a comparative aqueous glycolic acid solution 7. The obtained comparative aqueous glycolic acid solution 7 had a water content of 19% by weight, a calculated monomeric glycolic acid weight ratio of 0.84 and a monomeric glycolic acid content of 65% by weight. Further, the comparative aqueous glycolic acid solution 7 contained, as impurities, 1.6% by weight of diglycolic acid, 0.8% by weight of methoxyacetic acid and 0.3% by weight of formic acid.

Dried glycolic acid crystals were obtained in substantially the same manner as in Example 5, except that the comparative aqueous glycolic acid solution 7 was used instead of the aqueous glycolic acid solution 3. The pressure filtration of the slurry containing the deposited crystals and the separation of the crystals by dehydration under a stream of air were able to be performed efficiently.

The yield of the obtained, dried glycolic acid crystals was 23% by weight, and the purity of the dried glycolic acid crystals was as low as 99.69% by weight.

COMPARATIVE EXAMPLE 5

1,230 g of comparative aqueous glycolic acid solution 6 produced in Comparative Example 1 and 41 g of glycolic acid crystals having a purity of 99.98% by weight (which contained, as impurities, 0.01% by weight of diglycolic acid and 0.01% by weight of methoxyacetic acid) were mixed together. The resultant mixture was subjected to dehydration/concentration under a stream of nitrogen gas under atmospheric pressure so as to lower the water content thereof to 27% by weight. Subsequently, the resultant mixture having a water content of 27% by weight was subjected to dehydration/concentration under reduced pressure, namely under a pressure of from 4 to 5 kPa, at 45° C. for 10 minutes, thereby obtaining a comparative aqueous glycolic acid solution 8. The obtained comparative aqueous glycolic acid solution 8 had a water content of 23% by weight, a calculated monomeric glycolic acid weight ratio of 0.75 and a monomeric glycolic acid content of 55% by weight. Further, the comparative aqueous glycolic acid solution 8 contained, as impurities, 1.4% by weight of diglycolic acid, 0.8% by weight of methoxyacetic acid and 0.3% by weight of formic acid.

Dried glycolic acid crystals were obtained in substantially the same manner as in Example 5, except that the comparative aqueous glycolic acid solution 8 was used instead of the aqueous glycolic acid solution 3, and the time for the deposition of the glycolic acid crystals was changed to −5° C. The pressure filtration of the slurry containing the deposited crystals and the separation of the crystals by dehydration under a stream of air were able to be performed efficiently.

The yield of the obtained, dried glycolic acid crystals was 14% by weight, and the purity of the dried glycolic acid crystals was as low as 99.72% by weight.

COMPARATIVE EXAMPLE 6

The temperature of the comparative aqueous glycolic acid solution 4 (1,000 g) was adjusted to 30° C. and, then, 30 g of water having a temperature of 30° C. was added to the comparative aqueous glycolic acid solution 4, followed by stirring mildly for 3 minutes, thereby obtaining a comparative aqueous glycolic acid solution 9. The obtained comparative aqueous glycolic acid solution 9 had a water content of 6% by weight, a calculated monomeric glycolic acid weight ratio of 1.02 and a monomeric glycolic acid content of 34% by weight. Further, the comparative aqueous glycolic acid solution 9 contained, as impurities, 1.9% by weight of diglycolic acid, 1.1% by weight of methoxyacetic acid and 0.2% by weight of formic acid.

Dried glycolic acid crystals were obtained in substantially the same manner as in Example 5, except that the comparative aqueous glycolic acid solution 9 was used instead of the aqueous glycolic acid solution 3. The pressure filtration of the slurry containing the deposited crystals and the separation of the crystals by dehydration under a stream of air were not able to be performed efficiently.

The yield of the obtained, dried glycolic acid crystals was 22% by weight, and the purity of the dried glycolic acid crystals was as low as 99.70% by weight.

EXAMPLE 6

A slurry was obtained in substantially the same manner as in Example 1, except that 420 g of the aqueous glycolic acid solution 2 was used instead of the aqueous glycolic acid solution 1, and that the temperature for the deposition of the glycolic acid crystals was changed to 10° C. The obtained slurry was subjected to pressure filtration under 0.3 MPa (in which air was used as a pressurizing medium) by means of a pressure filtration apparatus using a filter paper (3250, manufactured and sold by Azumi Filter Paper Co., Ltd., Japan). After completion of a continuous discharge of the filtrate, the resultant residue was subjected to dehydration under a stream of air for 10 minutes, thereby separating crystals (hereinafter, referred to as "crystals 1"). The discharged filtrate was recovered.

A part (262 g) of the recovered filtrate was mixed with 211 g of the above-mentioned commercially available aqueous glycolic acid solution and, then, the resultant mixture was subjected to dehydration/concentration under a stream of nitrogen gas under atmospheric pressure at 111 to 120° C. for 35 minutes, thereby obtaining 420 g of an aqueous glycolic acid solution 10 (i.e., aqueous glycolic acid solution (A) used in the present invention). The obtained aqueous glycolic acid solution 10 had a water content of 14% by weight, a calculated monomeric glycolic acid weight ratio of 0.90 and a monomeric glycolic acid content of 51% by weight. Further, the aqueous glycolic acid solution 10 contained, as impurities, 2.0% by weight of diglycolic acid, 1.2% by weight of methoxyacetic acid and 0.2% by weight of formic acid.

The aqueous glycolic acid solution 10 was subjected to substantially the same operations (i.e., the deposition, the filtration and the dehydration under a stream of air) as performed for obtaining the above-mentioned crystals 1, thereby separating crystals (hereinafter, referred to as "crystals 2") from the aqueous glycolic acid solution 10.

The removal of impurities from the crystals 1 was performed as follows. The crystals 1 were fed to an eggplant type flask which had an internal volume of 300 ml and, then, 100 ml of the washing solution 1 was fed to the eggplant type flask, followed by stirring at 5° C. for 30 minutes. The resultant was subjected to pressure filtration in the same manner as mentioned above (pressure=0.3 MPa, pressurizing medium=air). After completion of a continuous discharge of the filtrate, the resultant residue was subjected to dehydration under a stream of air for 10 minutes, thereby separating the crystals.

A series of the above-mentioned operations (i.e., the washing, the pressure filtration and the dehydration under a stream of air) for removing impurities was repeated once more, thereby obtaining purified crystals 1.

Subsequently, the purified crystals were subjected to vacuum drying at 35° C. until the weight of the crystals became constant, thereby obtaining final dried glycolic acid crystals.

On the other hand, the removal of impurities from the crystals 2 was performed in the same manner as in the removal of impurities from the crystals 1 (i.e., by repeating a series of the above-mentioned operations (i.e., the washing, the pressure filtration and the dehydration under a stream of air) twice), and the resultant purified crystals 2 were dried in the same manner as in the drying of the purified crystals 1, thereby obtaining final dried glycolic acid crystals.

With respect to each of the crystals 1 and 2, the pressure filtration and the separation of the crystals by dehydration under a stream of air were able to be performed efficiently. The yield of the final dried glycolic acid crystals obtained from the crystals 1 and the yield of the final dried glycolic acid crystals obtained from the crystals 2 were the same. Specifically, each of the above-mentioned yields was 22% by weight. Further, the purity of the final dried glycolic acid crystals obtained from the crystals 1 and the purity of the final dried glycolic acid crystals obtained from the crystals 2 were also the same. Specifically, each of the above-mentioned purities was 99.97% by weight. Thus, the recycle of the mother liquor had not caused either the lowering of the yield or the lowering of the purity.

EXAMPLE 7

Two types of dried glycolic acid crystals were obtained in substantially the same manner as in Example 6, except that the washing solution 3 was used instead of the washing solution 1, and that the temperature and time for the washing were changed to 55° C. and 20 minutes, respectively.

With respect to each of the two types of crystals, the pressure filtration of the slurry and the separation of the crystals by dehydration under a stream of air were able to be performed efficiently.

The yields of the two types of dried glycolic acid crystals were the same. Specifically, each of the above-mentioned yields was 22% by weight. Further, the purities of the two types of dried glycolic acid crystals were also the same. Specifically, each of the above-mentioned purities was 99.99% by weight. Thus, the recycle of the mother liquor had not caused either the lowering of the yield or the lowering of the purity.

EXAMPLE 8

A slurry was obtained in substantially the same manner as in Example 1, except that 600 g of the aqueous glycolic acid solution 2 was used instead of the aqueous glycolic acid solution 1, and that the temperature for the deposition of the glycolic acid crystals was changed to 10° C. The obtained slurry was subjected to pressure filtration under 0.3 MPa (in which air was used as a pressurizing medium) by means of a pressure filtration apparatus using a filter paper (3250, manufactured and sold by Azumi Filter Paper Co., Ltd., Japan). After completion of a continuous discharge of the filtrate, the resultant residue was subjected to dehydration under a stream of air for 10 minutes, thereby separating crystals (hereinafter, referred to as "crystals 3"). The discharged filtrate was recovered.

The recovered filtrate was subjected to dehydration/concentration under a stream of nitrogen gas under atmospheric pressure at 112 to 125° C. for 40 minutes, thereby obtaining an aqueous glycolic acid solution 11 (i.e., aqueous glycolic acid solution (A) used in the present invention). The obtained aqueous glycolic acid solution 11 had a water content of 13% by weight, a calculated monomeric glycolic acid weight ratio of 0.91 and a monomeric glycolic acid content of 51% by weight. Further, the aqueous glycolic acid solution 11 contained, as impurities, 2.2% by weight of diglycolic acid, 1.3% by weight of methoxyacetic acid and 0.2% by weight of formic acid.

The aqueous glycolic acid solution 11 was subjected to substantially the same operations (i.e., the deposition, the filtration and the dehydration under a stream of air) as performed for obtaining the above-mentioned crystals 3, thereby separating crystals (hereinafter, referred to as "crystals 4") from the aqueous glycolic acid solution 11.

The removal of impurities from the crystals 3 was performed as follows. The crystals 3 were fed to an eggplant type flask which had an internal volume of 300 ml and, then, 100 ml of the washing solution 1 was fed to the eggplant type flask, followed by stirring at 5° C. for 30 minutes. The resultant was subjected to pressure filtration in the same manner as mentioned above (pressure=0.3 MPa, pressurizing medium=air). After completion of a continuous discharge of the filtrate, the resultant residue was subjected to dehydration under a stream of air for 10 minutes, thereby separating the crystals.

A series of the above-mentioned operations (i.e., the washing, the pressure filtration and the dehydration under a stream of air) for removing impurities was repeated once more, thereby obtaining purified crystals 3.

Subsequently, the purified crystals were subjected to vacuum drying at 35° C. until the weight of the crystals became constant, thereby obtaining final dried glycolic acid crystals.

On the other hand, the removal of impurities from the crystals 4 was performed in the same manner as in the removal of impurities from the crystals 3 (i.e., by repeating a series of the above-mentioned operations (i.e., the washing, the pressure filtration and the dehydration under a stream of air) twice), and the resultant purified crystals 4 were dried in the same manner as in the drying of the purified crystals 3, thereby obtaining final dried glycolic acid crystals.

With respect to each of the crystals 3 and 4, the pressure filtration and the separation of the crystals by dehydration under a stream of air were able to be performed efficiently. The yield of the final dried glycolic acid crystals obtained from the crystals 3 and the yield of the final dried glycolic acid crystals obtained from the crystals 4 were the same. Specifically, each of the above-mentioned yields was 22% by weight. Further, the purity of the final dried glycolic acid crystals obtained from the crystals 3 and the purity of the final dried glycolic acid crystals obtained from the crystals 4 were also the same. Specifically, each of the above-mentioned purities was 99.97% by weight. Thus, the recycle of the mother liquor had not caused either the lowering of the yield or the lowering of the purity.

EXAMPLE 9

Dried glycolic acid crystals were obtained in substantially the same manner as in Example 1, except that the aqueous glycolic acid solution 5 was used instead of the aqueous glycolic acid solution 1, and that the temperature for the deposition of the glycolic acid crystals was changed to 10° C. The vacuum filtration of the slurry containing the deposited crystals and the separation of the crystals by dehydration under a stream of air were able to be performed efficiently.

The yield of the obtained, dried glycolic acid crystals was 23% by weight, and the purity of the dried glycolic acid crystals was 99.97% by weight. Further, the obtained, dried glycolic acid crystals contained, as impurities, sodium chloride and the like; however, since the impurity content of the dried glycolic acid crystals was as low as 0.03% by weight (wherein the sodium chloride content was not more than 50 ppm), there was no need for a further purification treatment, such as an ion exchange resin treatment.

EXAMPLE 10

Using the dried glycolic acid crystals obtained in the Examples and the Comparative Examples, glycolic acid-lactic acid copolymer resins were produced as described below.

RESIN PRODUCTION EXAMPLE 1

To a pyrex glass separable flask which had an internal volume of 100 ml and was equipped with a distillation tube and a stirrer were fed 76 g of the dried glycolic acid crystals obtained in Example 1 and 10.0 g of a 90% by weight aqueous solution of L-lactic acid (manufactured and sold by PURAC, Netherlands), followed by addition of 0.07% by weight of tetraisopropoxy germanium, based on the total weight of the above-mentioned dried glycolic acid crystals and aqueous solution, to thereby obtain a mixture. The flask was purged with nitrogen gas. Subsequently, the temperature of the mixture in the flask was elevated from 130° C. to 150° C. over 80 minutes and, then, maintained at 150° C. for 40 minutes, thereby performing dehydration of the mixture. After the dehydration, the internal pressure of the flask was reduced from $1.013 \times 10^5$ Pa to $1.333 \times 10^2$ Pa over 3 hours while maintaining the temperature of the mixture in the flask at 150° C. and, then, maintained at $1.333 \times 10^2$ Pa for 1 hour, thereby performing a condensation reaction while removing by-produced water. Subsequently, the temperature of the resultant reaction mixture in the flask was elevated to 200° C. and the condensation reaction was continued under reduced pressure, namely, under a pressure of $1.333 \times 10^2$ Pa for 7 hours. After completion of the condensation reaction, the resultant reaction mixture was subjected to heat treatment at 130° C. for 2 hours while maintaining the internal pressure of the flask at $1.333 \times 10^2$ Pa, thereby obtaining glycolic acid-lactic acid copolymer crystals (hereinafter, referred to as "crystal prepolymer"). The crystal prepolymer had a weight average molecular weight of 33,000 and melting peak temperatures of 160° C. and 181° C. as measured by the above-mentioned DSC method.

The obtained crystal prepolymer was placed in a mortar and crushed with a pestle. The resultant particles were passed through a sieve to obtain prepolymer particles having diameters in the range of from 100 to 300 μm.

0.5 g of the obtained prepolymer particles was fed to a pyrex glass U-tube, and a solid-phase polymerization reaction was performed under $1.013 \times 10^5$ Pa at 170° C. for 30 hours, while flowing nitrogen gas having a dew point of −85° C. at a rate of 0.8 N liter/min, thereby obtaining a glycolic acid-lactic acid copolymer resin.

The weight average molecular weight of the obtained copolymer resin was measured. The result is shown in Table 1.

RESIN PRODUCTION EXAMPLE 2

A glycolic acid-lactic acid copolymer resin was produced in substantially the same manner as in Resin Production Example 1, except that the dried glycolic acid crystals obtained in Example 2 were used instead of the dried glycolic acid crystals obtained in Example 1. The weight average molecular weight of the produced copolymer resin was measured. The result is shown in Table 1.

RESIN PRODUCTION EXAMPLE 3

A glycolic acid-lactic acid copolymer resin was produced in substantially the same manner as in Resin Production Example 1, except that the dried glycolic acid crystals obtained in Example 3 were used instead of the dried glycolic acid crystals obtained in Example 1. The weight average molecular weight of the produced copolymer resin was measured. The result is shown in Table 1.

RESIN PRODUCTION EXAMPLE 4

A glycolic acid-lactic acid copolymer resin was produced in substantially the same manner as in Resin Production Example 1, except that the dried glycolic acid crystals obtained in Example 4 were used instead of the dried glycolic acid crystals obtained in Example 1. The weight average molecular weight of the produced copolymer resin was measured. The result is shown in Table 1.

RESIN PRODUCTION EXAMPLE 5

A glycolic acid-lactic acid copolymer resin was produced in substantially the same manner as in Resin Production Example 1, except that the dried glycolic acid crystals obtained in Example 5 were used instead of the dried glycolic acid crystals obtained in Example 1. The weight average molecular weight of the produced copolymer resin was measured. The result is shown in Table 1.

RESIN PRODUCTION EXAMPLE 6

A glycolic acid-lactic acid copolymer resin was produced in substantially the same manner as in Resin Production Example 1, except that the dried glycolic acid crystals obtained in Comparative Example 1 were used instead of the dried glycolic acid crystals obtained in Example 1, and the solid-phase polymerization reaction time was changed to 30 hours. Further, another glycolic acid-lactic acid copolymer resin was produced in substantially the same manner as mentioned above, except that the solid-phase polymerization reaction time was changed to 50 hours. The weight average molecular weight of each of the produced copolymer resins was measured. The results are shown in Table 1.

RESIN PRODUCTION EXAMPLE 7

A glycolic acid-lactic acid copolymer resin was produced in substantially the same manner as in Resin Production Example 1, except that the dried glycolic acid crystals obtained in Comparative Example 2 were used instead of the dried glycolic acid crystals obtained in Example 1, and that the solid-phase polymerization reaction time was changed to 30 hours. Further, another glycolic acid-lactic acid copolymer resin was produced in substantially the same manner as mentioned above, except that the solid-phase polymerization reaction time was changed to 50 hours. The weight average molecular weight of each of the produced copolymer resins was measured. The results are shown in Table 1.

RESIN PRODUCTION EXAMPLE 8

A glycolic acid-lactic acid copolymer resin was produced in substantially the same manner as in Resin Production Example 1, except that the dried glycolic acid crystals obtained in Comparative Example 3 were used instead of the dried glycolic acid crystals obtained in Example 1, and the solid-phase polymerization reaction time was changed to 30 hours. Further, another glycolic acid-lactic acid copolymer resin was produced in substantially the same manner as mentioned above, except that the solid-phase polymerization reaction time was changed to 50 hours. The weight average molecular weight of each of the produced copolymer resins was measured. The results are shown in Table 1.

RESIN PRODUCTION EXAMPLE 9

A glycolic acid-lactic acid copolymer resin was produced in substantially the same manner as in Resin Production Example 1, except that the dried glycolic acid crystals obtained in Comparative Example 4 were used instead of the dried glycolic acid crystals obtained in Example 1, and that the solid-phase polymerization reaction time was changed to 30 hours. Further, another glycolic acid-lactic acid copolymer resin was produced in substantially the same manner as mentioned above, except that the solid-phase polymerization reaction time was changed to 50 hours. The weight average molecular weight of each of the produced copolymer resins was measured. The results are shown in Table 1.

RESIN PRODUCTION EXAMPLE 10

A glycolic acid-lactic acid copolymer resin was produced in substantially the same manner as in Resin Production Example 1, except that the dried glycolic acid crystals obtained in Comparative Example 5 were used instead of the dried glycolic acid crystals obtained in Example 1, and that the solid-phase polymerization reaction time was changed to 30 hours. Further, another glycolic acid-lactic acid copolymer resin was produced in substantially the same manner as mentioned above, except that the solid-phase polymerization reaction time was changed to 50 hours. The weight average molecular weight of each of the produced copolymer resins was measured. The results are shown in Table 1.

RESIN PRODUCTION EXAMPLE 11

A glycolic acid-lactic acid copolymer resin was produced in substantially the same manner as in Resin Production Example 1, except that the dried glycolic acid crystals obtained in Comparative Example 6 were used instead of the dried glycolic acid crystals obtained in Example 1, and the solid-phase polymerization reaction time was changed to 30 hours. Further, another glycolic acid-lactic acid copolymer resin was produced in substantially the same manner as mentioned above, except that the solid-phase polymerization reaction time was changed to 50 hours. The weight average molecular weight of each of the produced copolymer resins was measured. The results are shown in Table 1.

RESIN PRODUCTION EXAMPLE 12

A glycolic acid-lactic acid copolymer resin was produced in substantially the same manner as in Resin Production Example 1, except that the dried glycolic acid crystals obtained in Example 6 were used instead of the dried glycolic acid crystals obtained in Example 1. The weight average molecular weight of the produced copolymer resin was measured. The result is shown in Table 1.

RESIN PRODUCTION EXAMPLE 13

A glycolic acid-lactic acid copolymer resin was produced in substantially the same manner as in Resin Production Example 1, except that the dried glycolic acid crystals obtained in Example 7 were used instead of the dried glycolic acid crystals obtained in Example 1. The weight average molecular weight of the produced copolymer resin was measured. The result is shown in Table 1.

RESIN PRODUCTION EXAMPLE 14

A glycolic acid-lactic acid copolymer resin was produced in substantially the same manner as in Resin Production Example 1, except that the dried glycolic acid crystals obtained in Example 8 were used instead of the dried glycolic acid crystals obtained in Example 1. The weight average molecular weight of the produced copolymer resin was measured. The result is shown in Table 1.

RESIN PRODUCTION EXAMPLE 15

A glycolic acid-lactic acid copolymer resin was produced in substantially the same manner as in Resin Production Example 1, except that the dried glycolic acid crystals obtained in Example 9 were used instead of the dried glycolic acid crystals obtained in Example 1. The weight average molecular weight of the produced copolymer resin was measured. The result is shown in Table 1.

TABLE 1

| Example | Purity of dried glycolic acid crystals used (% by weight) | Solid-phase polymerization reaction time (hr) | Weight average molecular weight of glycolic acid-lactic acid copolymer resin produced |
|---|---|---|---|
| Resin Production Example 1 | 99.96 | 30 | 180,000 |
| Resin Production Example 2 | 99.96 | 30 | 185,000 |
| Resin Production Example 3 | 99.97 | 30 | 186,000 |
| Resin Production Example 4 | 99.92 | 30 | 160,000 |
| Resin Production Example 5 | 99.90 | 30 | 152,000 |
| Resin Production Example 6 | 99.47 | 30 | 50,000 |
|  |  | 50 | 49,000 |
| Resin Production Example 7 | 99.55 | 30 | 55,000 |
|  |  | 50 | 53,000 |
| Resin Production Example 8 | 99.68 | 30 | 80,000 |
|  |  | 50 | 81,000 |
| Resin Production Example 9 | 99.69 | 30 | 81,000 |
|  |  | 50 | 82,000 |
| Resin Production Example 10 | 99.72 | 30 | 88,000 |
|  |  | 50 | 88,000 |
| Resin Production Example 11 | 99.70 | 30 | 84,000 |
|  |  | 50 | 85,000 |
| Resin Production Example 12 | 99.97 | 30 | 185,000 |
| Resin Production Example 13 | 99.99 | 30 | 210,000 |
| Resin Production Example 14 | 99.97 | 30 | 183,000 |
| Resin Production Example 15 | 99.97 | 30 | 184,000 |

INDUSTRIAL APPLICABILITY

By the method of the present invention, it becomes possible to produce high purity glycolic acid crystals easily and in high yield on a commercial scale, which high purity glycolic acid crystals can be advantageously used for producing a glycolic acid polymer having a high molecular weight, and the like.

The invention claimed is:

1. A method for producing high purity glycolic acid crystals from an aqueous glycolic acid solution, which comprises the steps of:
   (1) providing an aqueous glycolic acid solution (A) containing monomeric glycolic acid and a glycolic acid condensation product, said aqueous glycolic acid solution (A) having the following characteristics (a), (b) and (c):
   (a) a water content of from 5 to 20% by weight,
   (b) a calculated monomeric glycolic acid weight ratio of from 0.60 to 1.00, said calculated monomeric glycolic acid weight ratio being defined as a ratio of the total weight of said monomeric glycolic acid and said glycolic acid condensation product to the weight of said aqueous solution (A), wherein the weight of said glycolic acid condensation product is expressed in terms of the weight of component monomeric glycolic acid of the glycolic acid condensation product, and
   (c) a monomeric glycolic acid content of from 20 to 57% by weight,
   (2) depositing glycolic acid crystals from said aqueous glycolic acid solution (A), and
   (3) recovering the deposited glycolic acid crystals from said aqueous glycolic acid solution (A).

2. The method according to claim 1, wherein the deposition of glycolic acid crystals from said aqueous glycolic acid solution (A) in said step (2) is performed at a temperature in the range of from −30 to 50° C.

3. The method according to claim 1, wherein the deposition of glycolic acid crystals from said aqueous glycolic acid solution (A) in said step (2) is performed in the presence of glycolic acid crystals as seed crystals.

4. The method according to any one of claims 1 to 3, which further comprises, after said step (3), the step of:
   (4) washing the separated glycolic acid crystals with an aqueous glycolic acid solution (B).

5. The method according to claim 4, wherein:

said aqueous glycolic acid solution (B) contains monomeric glycolic acid and optionally a glycolic acid condensation product, and said aqueous glycolic acid solution (B) satisfies the following formulae (I) and (II):

$$0.0055 \times T + 0.3 \leq W \leq 0.0072 \times T + 0.8 \quad \text{(I)}$$

and $$-5 \leq T \leq 70 \quad \text{(II)}$$

wherein:

W represents a calculated monomeric glycolic acid weight ratio of the aqueous solution (B), said calculated monomeric glycolic acid weight ratio being defined as a ratio of the total weight of said monomeric glycolic acid and said glycolic acid condensation product to the weight of said aqueous solution (B), wherein the weight of said glycolic acid condensation product is expressed in terms of the weight of component monomeric glycolic acid of the glycolic acid condensation product, and T represents the temperature (° C.) of the aqueous solution (B).

* * * * *